United States Patent
Bissell et al.

(10) Patent No.: US 6,235,493 B1
(45) Date of Patent: May 22, 2001

(54) AMINO ACID SUBSTITUTED-CRESYL VIOLET, SYNTHETIC FLUOROGENIC SUBSTRATES FOR THE ANALYSIS OF AGENTS IN INDIVIDUAL IN VIVO CELLS OR TISSUE

(75) Inventors: Eugene R. Bissell, Alamo; Robert F. Smith, Livermore, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/130,193

(22) Filed: Aug. 5, 1998

Related U.S. Application Data
(60) Provisional application No. 60/055,392, filed on Aug. 6, 1997.

(51) Int. Cl.[7] .............................. C12Q 1/37; G01N 21/64; C07D 265/34
(52) U.S. Cl. .............................. 435/24; 435/23; 436/172; 544/199
(58) Field of Search .......................... 435/24, 212, 40.51, 435/40.52, 23; 436/172; 530/330; 544/99

(56) References Cited

U.S. PATENT DOCUMENTS

| | | | | |
|---|---|---|---|---|
| 3,769,173 | * | 10/1973 | Carroll | 195/103.5 |
| 4,771,123 | * | 9/1988 | Cho et al. | 530/323 |
| 5,601,986 | * | 2/1997 | Takacs | 435/7.4 |

OTHER PUBLICATIONS

Cornelis J. F. Van Noorden et al., "Heterogeneous suppression of experimentally induced colon cancer metastasis in rat liver lobes by inhibition of extracellular cathepsin B", *Clinical Experimental Metastasis*, vol. 16; pp. 159–167, (1998).

(List continued on next page.)

*Primary Examiner*—Ardin H. Marschel
*Assistant Examiner*—Marjorie A. Moran
(74) *Attorney, Agent, or Firm*—Peters Verny Jones & Biksa, LLP

(57) ABSTRACT

The present invention concerns a method to detect the presence of an enzyme in in vivo or in vitro tissue or cell, which method comprises:
(a) obtaining a tissue or cell sample to be analyzed;
(b) contacting the tissue or cell sample with a substrate of the structure selected from the group consisting of:

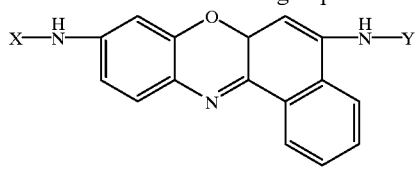

X=H or one or more natural or synthetic amino acids with or without amino blocking groups,
Y=H or one or more natural or synthetic amino acids with or without amino blocking groups,
wherein X and Y are the same or different and are amino acid sequences of between about 1 to 1,000,000 amino acids wherein each amino acid is the same or a different amino acid, with the proviso that at least one of X or Y is at least one amino acid;
(c) when an enzyme is present in the tissue or cell sample which degrades X, Y and combinations thereof, fluorescent cresyl violet is released in the tissue sample producing a color change;
(d) detecting the presence and amount of the enzyme present by the detection and quantification of the fluorescence produced; and
(e) optionally comparing the fluorescence to a pre-calibrated fluorescence scale to quantify the fluorescence present. A diagnostic kit for use and a method to prepare amino acid cresyl violet derivatives are described.

18 Claims, 8 Drawing Sheets

(2 of 8 Drawing Sheet(s) Filed in Color)

OTHER PUBLICATIONS

Robert E. Smith et al., "The significance of hypersialylation of dipeptidyl peptidase IV (CD26) in the inhibition of its activity by tat and other cationic peptides", *Aids Research and Human Retroviruses* vol. 14; pp. 851–868, (1998).

Cornelis J. F. Van Noorden et al., Ala–Pro–Cresyl Violet, a synthetic fluorogenic substrate for the analysis of kinetic parameters of dipeptidyl peptidase IV (CD26) in individual living rat hepatocytes, *Analytical Biochemistry*, vol. 252, pp. 71–77, (Oct. 1997).

Marupudi Sivaparvathi et al., "Overexpression and localization of cathepsin B during the progression of human gliomas", *Clinical & Experimental Metastasis*, vol. 13, pp. 49–56, (1995).

Bogdan Boduszek et al., "Dipeptide phosphonates as Inhibitors of Dipeptidyl Peptidase IV", *Journal of Medicinal Chemistry*, vol. 37, pp. 3969–3976 (1994).

Robert E. Smith et al. "The evolution of proteinase substrates with special reference to dipeptidylpeptidase IV", *Histochemical Journal* vol. 24; pp. 637–647 (1992).

Cornelis J. F. Van Noorden et al., "Cysteine proteinase activity in arthritic rat knee joints and the effe cts of a selective systemic inhibitor, Z–Phe–AlaCH$_2$F", *the Journal of Rheumatology*, vol. 15 (#10), pp. 1525–1535 (1988).

* cited by examiner

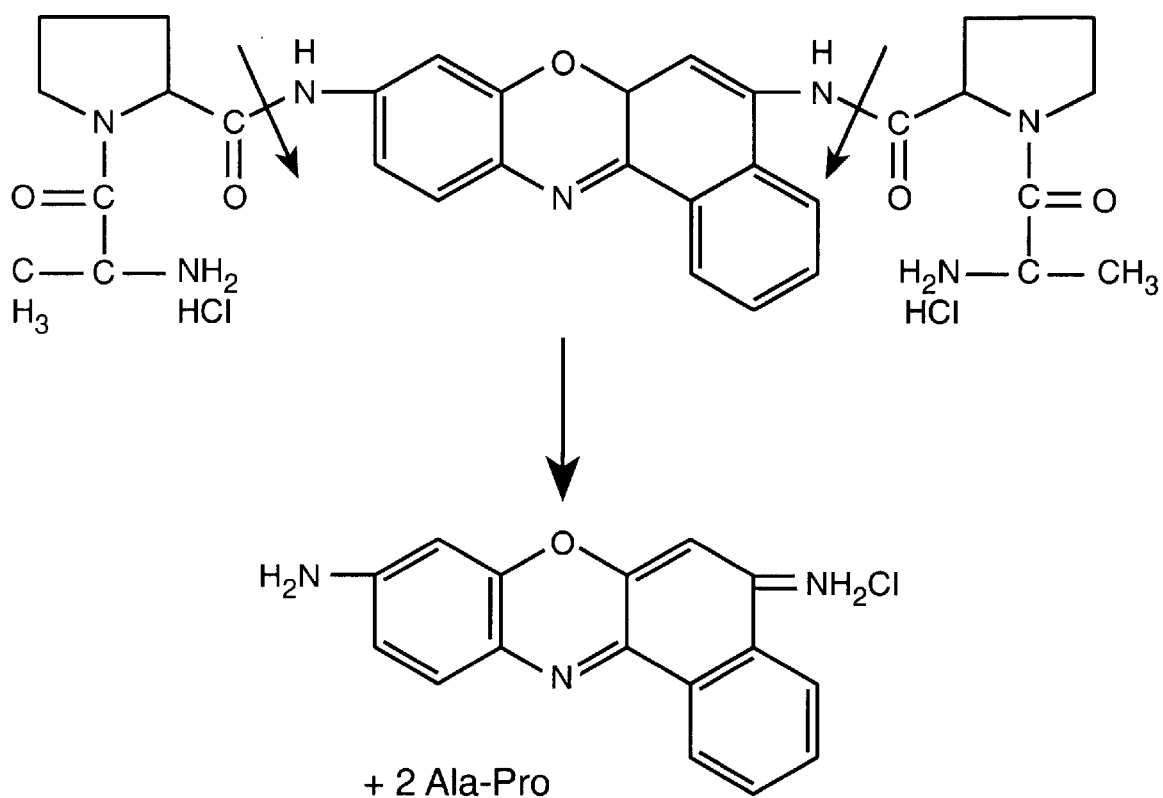
FIG._1

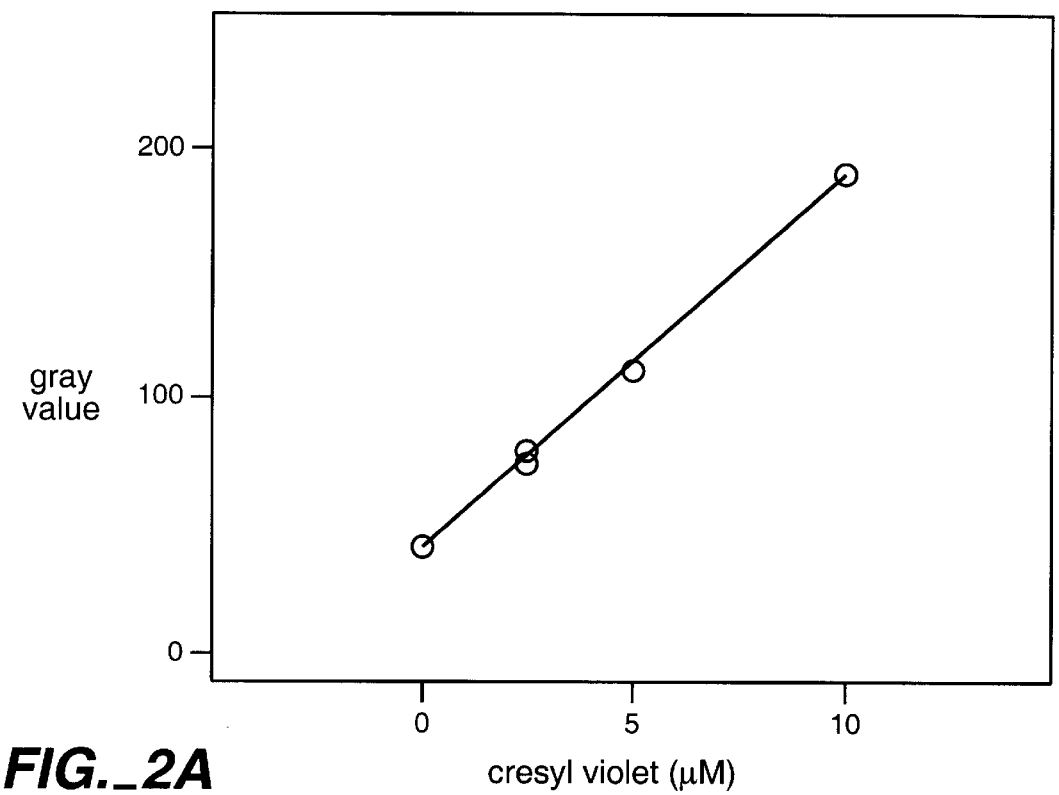
FIG._2A
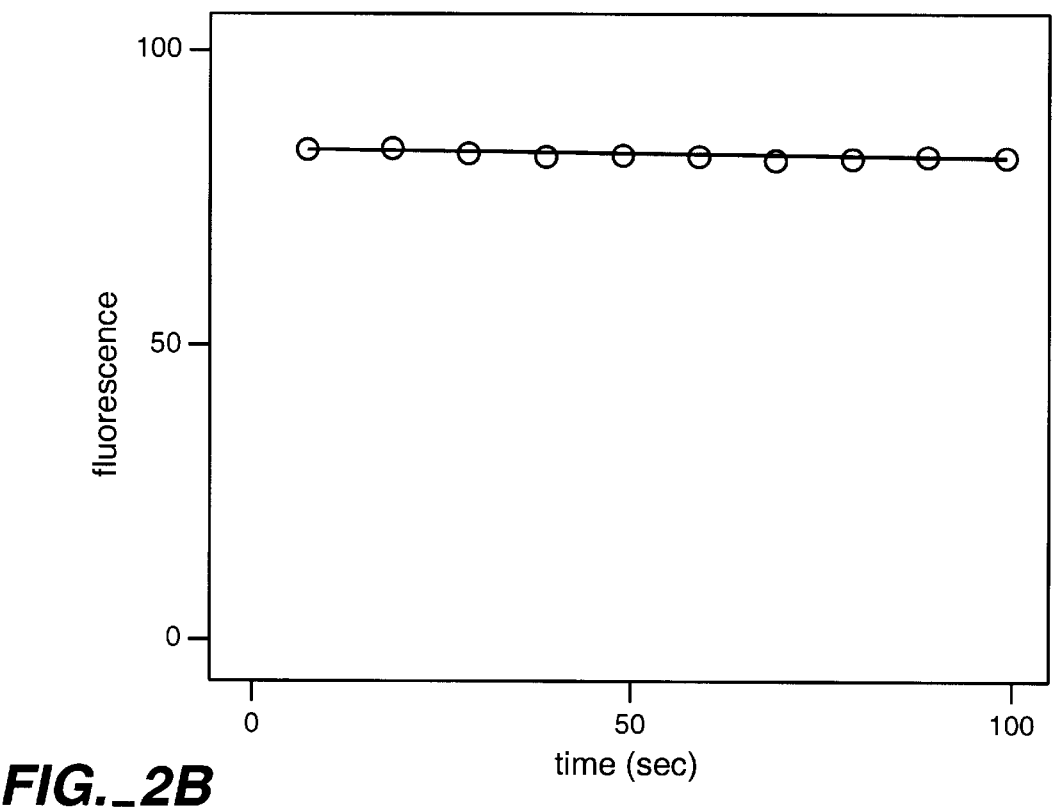
FIG._2B

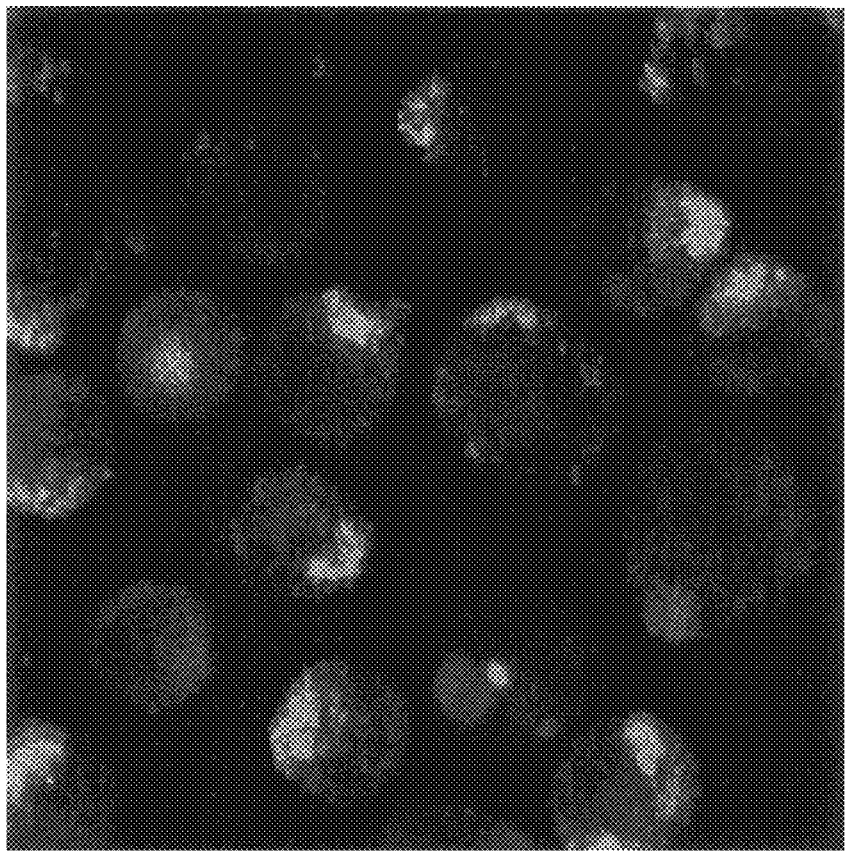
FIG._3
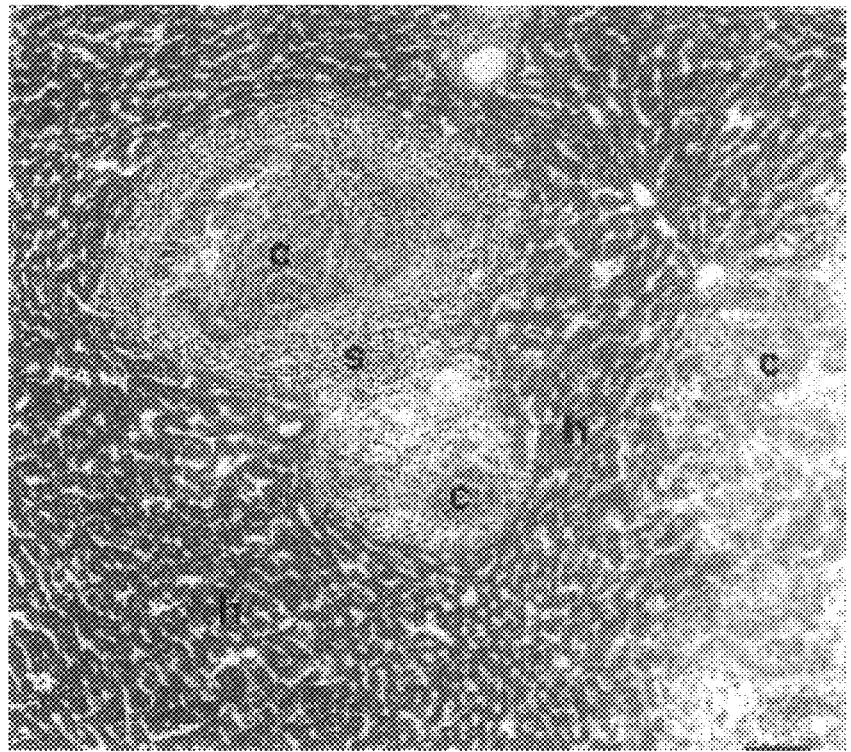
FIG._10

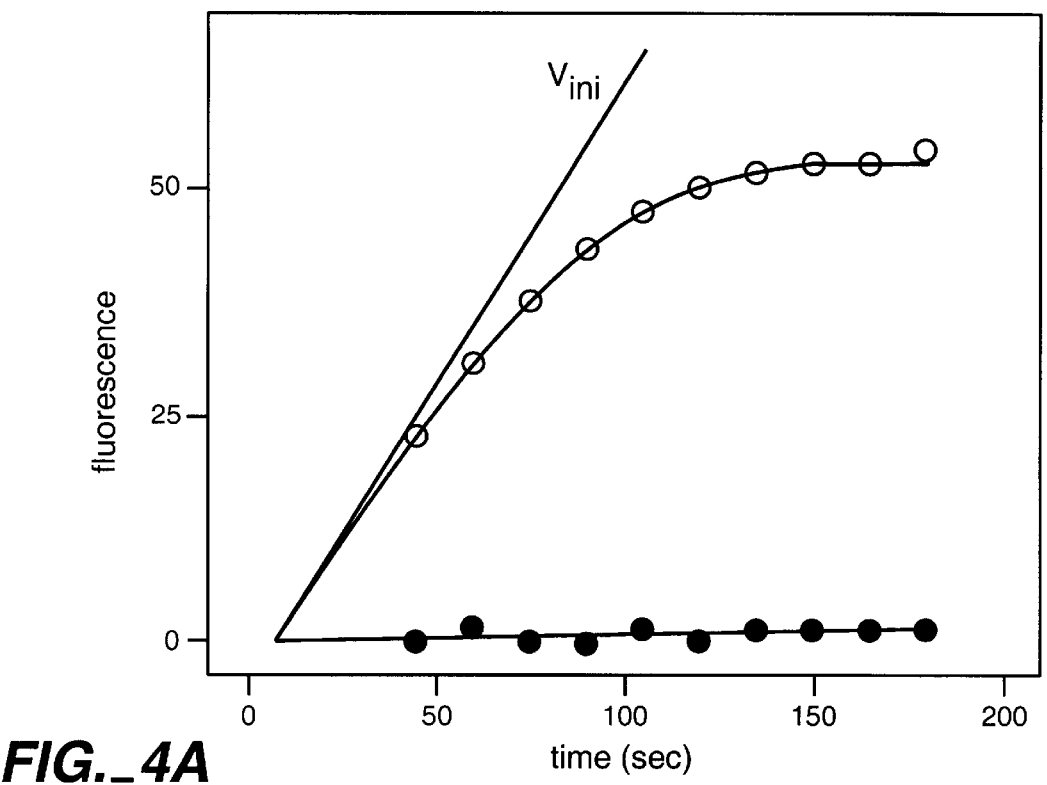
FIG._4A
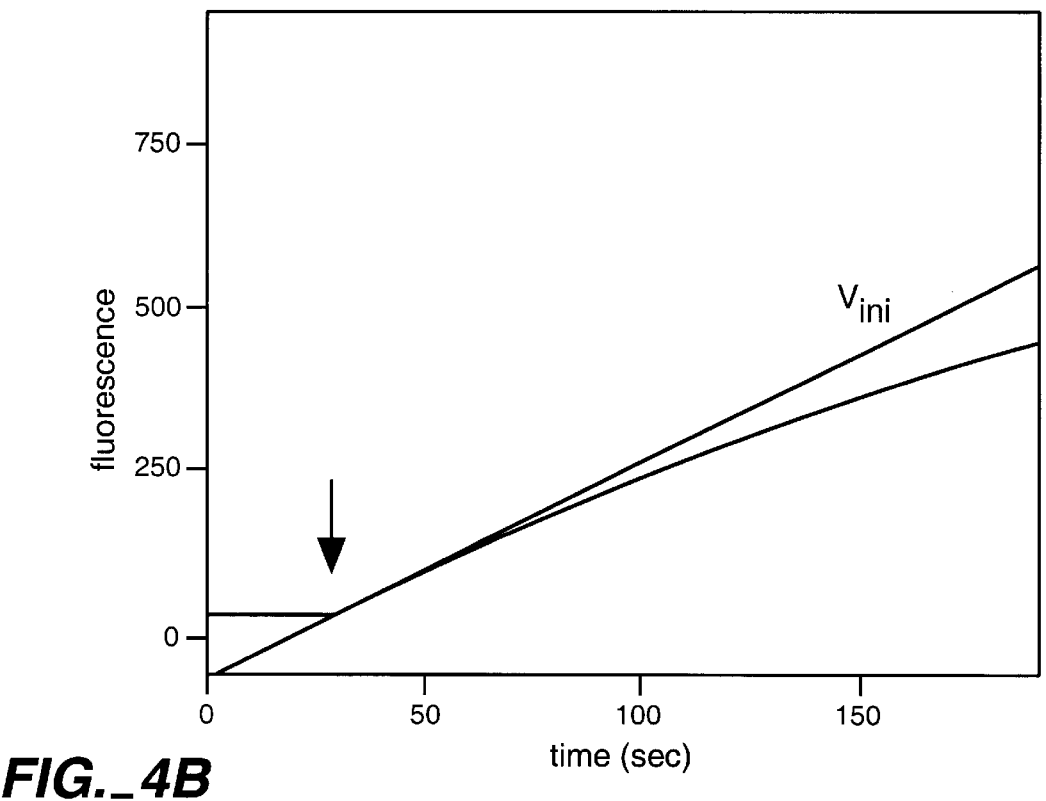
FIG._4B

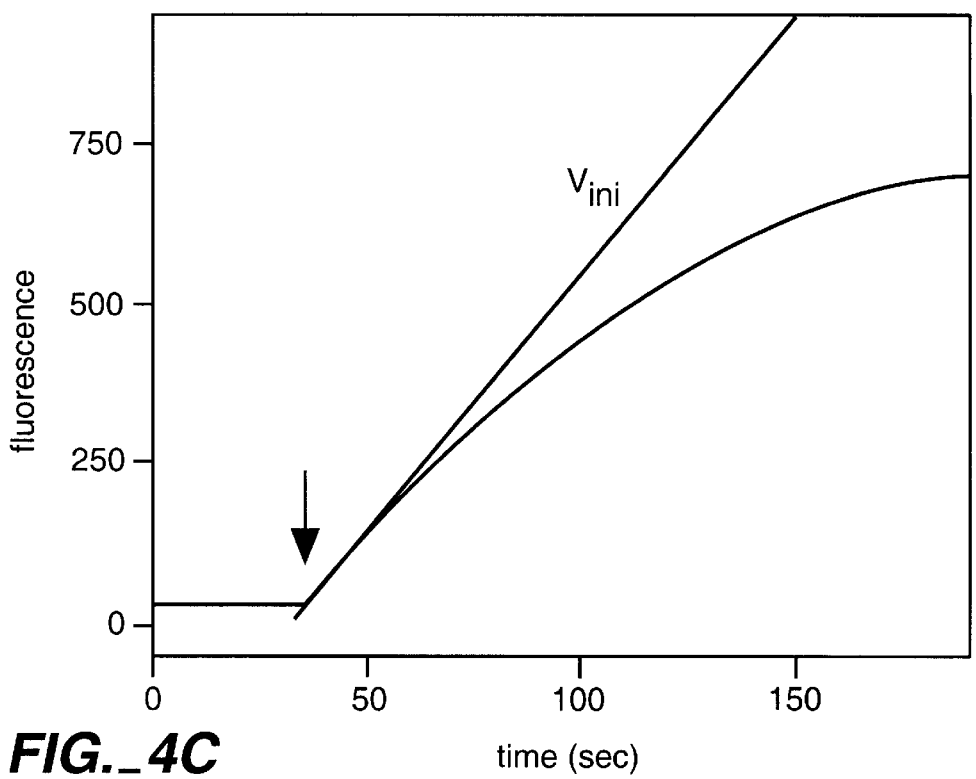
FIG._4C
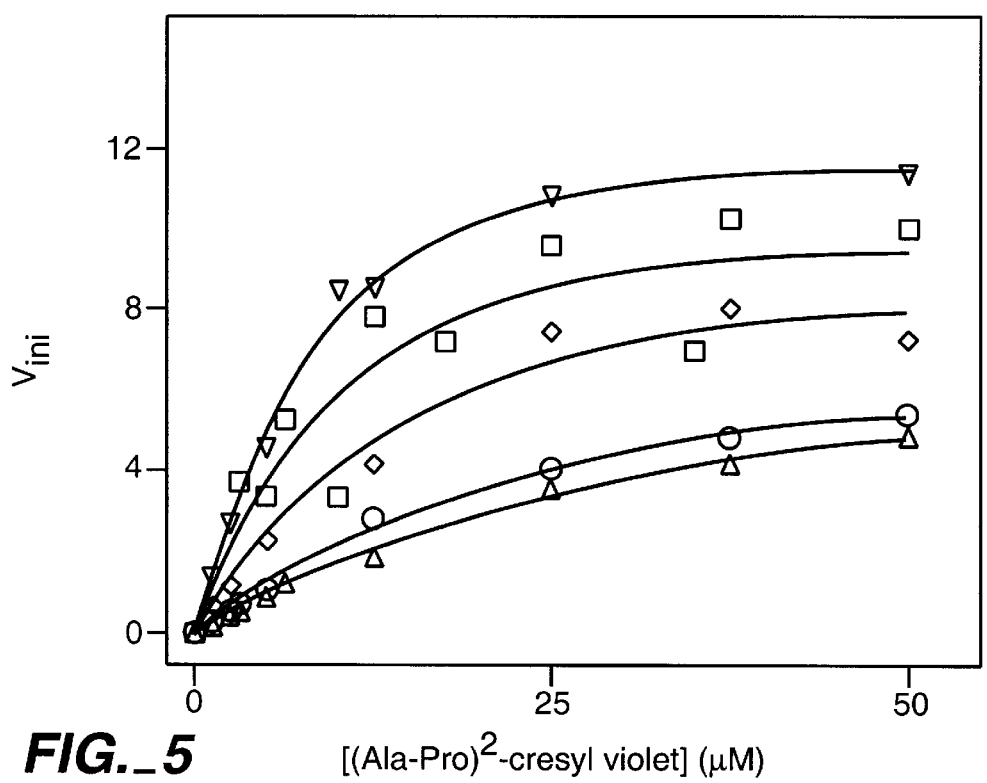
FIG._5

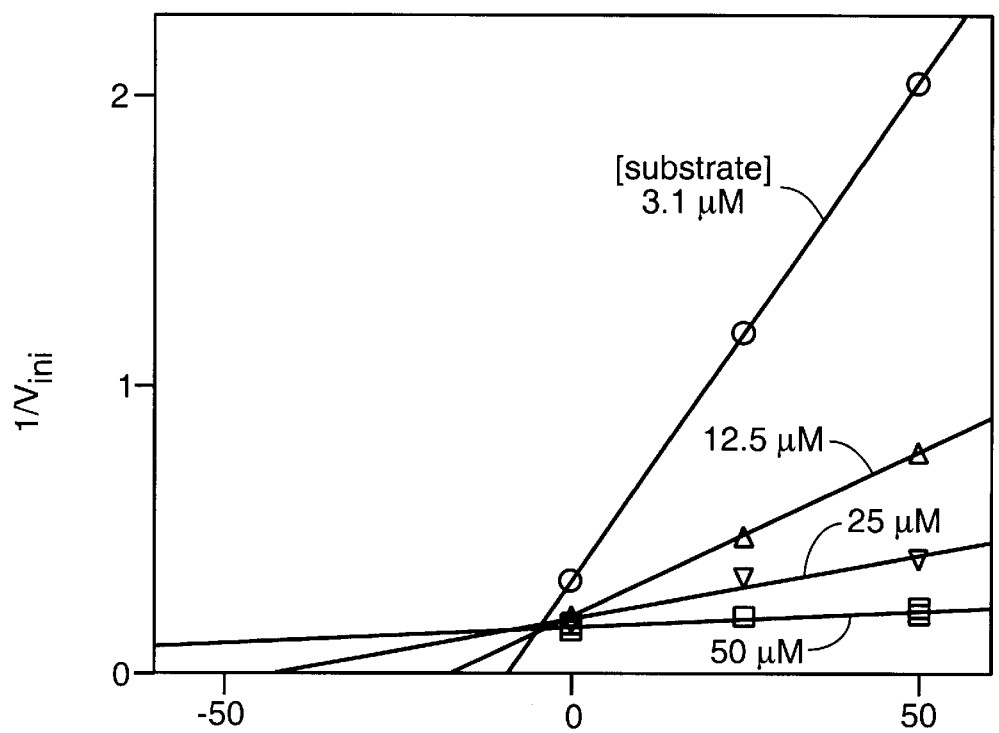
FIG._6
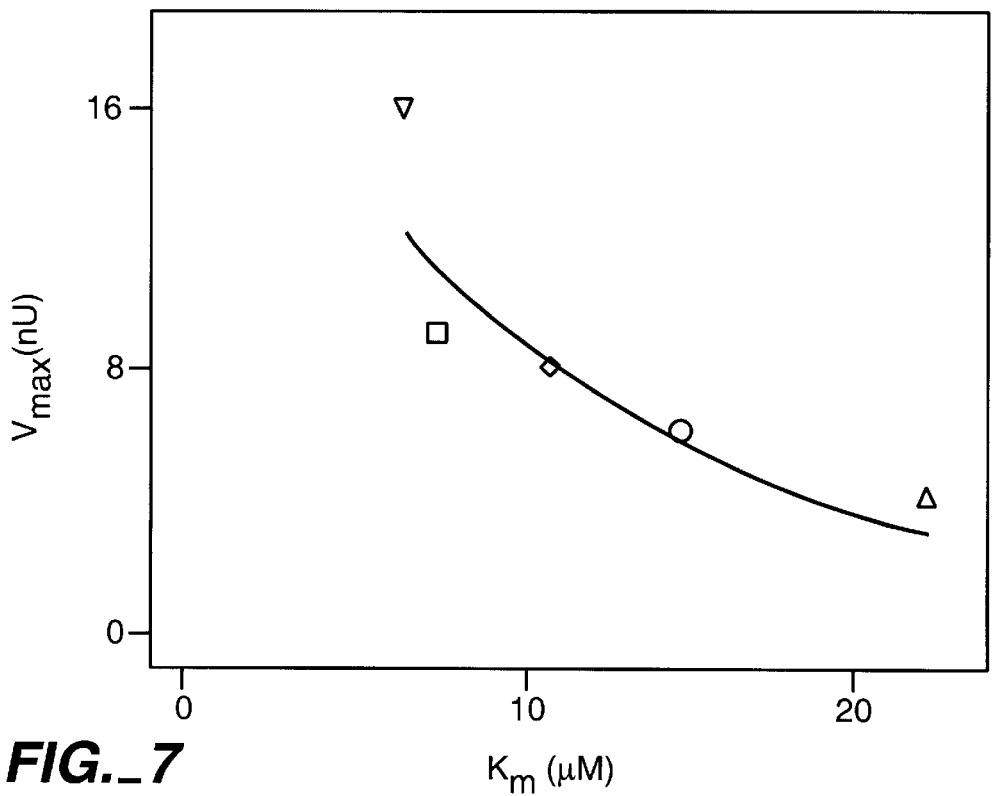
FIG._7

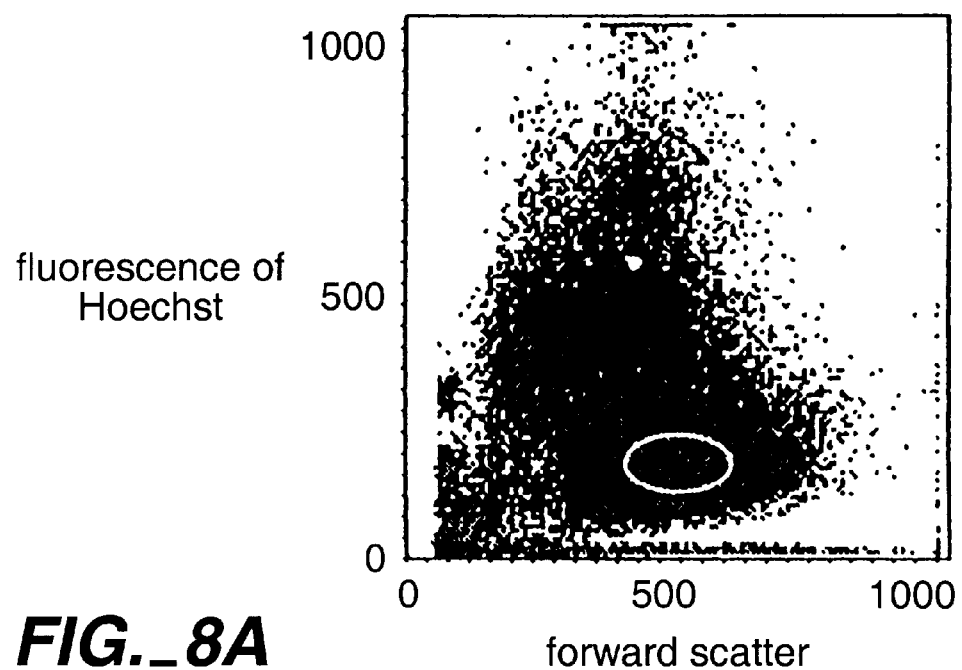
FIG._8A
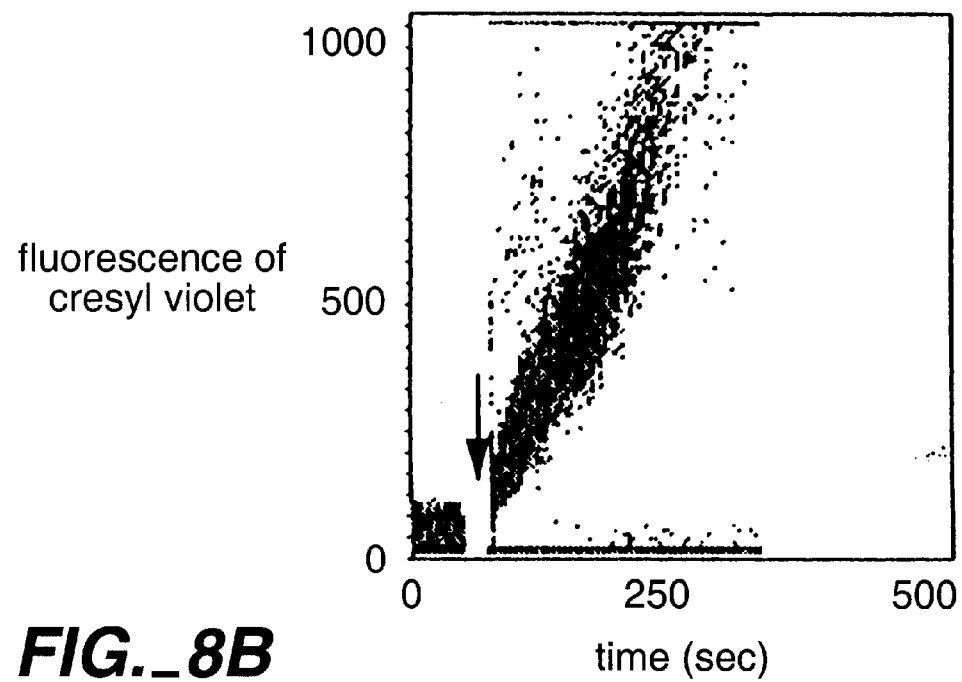
FIG._8B

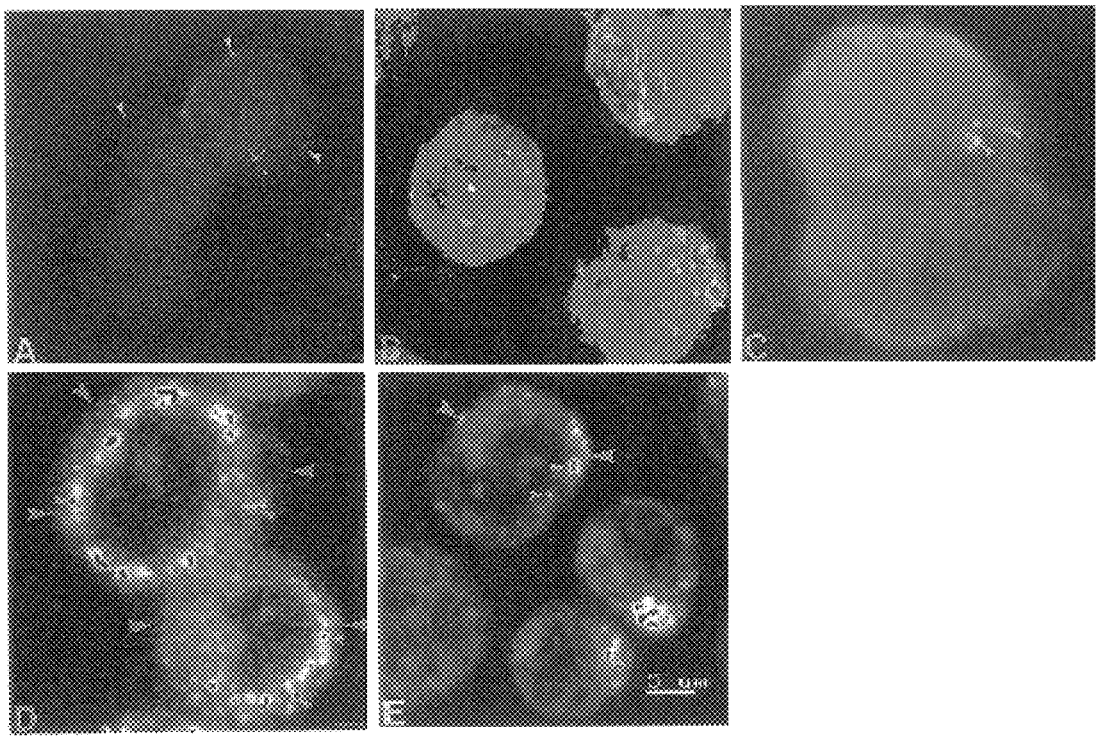

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) SEQUENCE DESCRIPTION: SEQ ID NO: 1:

Asp Glu Val Asp
 1

(2) INFORMATION FOR SEQ ID NO: 2:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) SEQUENCE DESCRIPTION: SEQ ID NO: 2:

Ile Glu Thr Asp
 1

(2) INFORMATION FOR SEQ ID NO: 3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) SEQUENCE DESCRIPTION: SEQ ID NO: 3:

Tyr Val Ala Asp
 1

(2) INFORMATION FOR SEQ ID NO: 4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) SEQUENCE DESCRIPTION: SEQ ID NO: 4:

Trp Glu His Asp
 1

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) SEQUENCE DESCRIPTION: SEQ ID NO: 5:

Val Asp Val Ala Asp
 1               5

(2) INFORMATION FOR SEQ ID NO: 6:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: protein (iii) SEQUENCE DESCRIPTION: SEQ ID NO: 6:

Val Asp Glu Gln Asp
 1               5

(2) INFORMATION FOR SEQ ID NO: 7:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: protein (iii) SEQUENCE DESCRIPTION: SEQ ID NO: 7:

Asp Glu Val Asp
 1

(2) INFORMATION FOR SEQ ID NO: 8:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: protein (iii) SEQUENCE DESCRIPTION: SEQ ID NO: 8:

Leu Glu Val Asp
 1

(2) INFORMATION FOR SEQ ID NO: 9:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: protein (iii) SEQUENCE DESCRIPTION: SEQ ID NO: 9:

Trp Glu His Asp
 1

(2) INFORMATION FOR SEQ ID NO: 10:

(i) SEQUENCE CHARACTERISTICS:
           (A) LENGTH: 4 amino acids
           (B) TYPE: amino acid
           (C) STRANDEDNESS: single (D) TOPOLOGY: linear (ii) MOLECULE TYPE: protein (iii) SEQUENCE DESCRIPTION: SEQ ID NO: 10:

Val Glu Ile Asp
 1

(2) INFORMATION FOR SEQ ID NO: 11:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) SEQUENCE DESCRIPTION: SEQ ID NO: 11:

Val Glu Val Asp
 1

(2) INFORMATION FOR SEQ ID NO: 12:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) SEQUENCE DESCRIPTION: SEQ ID NO: 12:

Asp Glu Val Asp
 1

(2) INFORMATION FOR SEQ ID NO: 13:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) SEQUENCE DESCRIPTION: SEQ ID NO: 13:

Ile Glu Thr Asp
 1

(2) INFORMATION FOR SEQ ID NO: 14:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) SEQUENCE DESCRIPTION: SEQ ID NO: 14:

Leu Glu His Asp
 1

(2) INFORMATION FOR SEQ ID NO: 15:

(i) SEQUENCE CHARACTERISTICS:
        (A) LENGTH: 4 amino acids
        (B) TYPE: amino acid

```
        (C) STRANDEDNESS: single
        (D) TOPOLOGY: linear (ii) MOLECULE TYPE: peptide (iii) SEQUENCE DESCRIPTION: SEQ ID NO: 15:

Asp Glu Val Asp
 1

(2) INFORMATION FOR SEQ ID NO: 16:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) SEQUENCE DESCRIPTION: SEQ ID NO: 16:

Ile Glu Pro Asp
```

AMINO ACID SUBSTITUTED-CRESYL VIOLET, SYNTHETIC FLUOROGENIC SUBSTRATES FOR THE ANALYSIS OF AGENTS IN INDIVIDUAL IN VIVO CELLS OR TISSUE

RELATED APPLICATION

This application is a continuation-in-part of U.S. Ser. No. 60/055,392, filed Aug. 6, 1997 which is incorporated herein by reference in its entirety.

FIELD OF THE INVENTION

The present invention concerns amino acid substituted-cresyl violet compounds such as (Ala-Pro)$^2$-cresyl violet and (CBZ-Arg)$^2$-cresyl violet, as synthetic fluorogenic, substrates for the analysis of kinetic parameters of enzymes in individual mammalian (i.e., human) cells or tissue.

DESCRIPTION OF RELATED ART

The art is discussed in two main areas. The first area is directed, the background concerning evaluation of the biochemical activity of extracellular cathepsin B in liver tissue. The second area is directed to the synthesis and use of an amino acid-cresyl violet agent to determine the kinetic parameters of dipeptidyl peptidase IV (CD26) in liver tissue.

Evaluation of Extra Cellular Cathepsin B

The references of interest are listed here and are found in the text below in parentheses.

1. C. S. He, et al. 1989. Tissue co-operation in a proteolytic cascade activating human interstitial collagenase. *Proc Natl Acad Sci USA*, 86, 2632–6.
2. L. A. Liotta, et al. 1991. Cancer metastasis and angiogenesis: an imbalance of positive and negative regulation. *Cell*, 64, 327–36.
3. H. Kobayashi, et al. 1993. Effects of membrane-associated cathepsin B on the activation of receptor-bound pro-urokinase and subsequent invasion of reconstituted basement membranes. *Biochem Biophys Acta*, 1178, 55–62.
4. C. Ruppert, et al. 1994. Proteases associated with gynecological tumours. *Int J Oncol*, 4, 717–21.
5. M. Sivaparvathi, et al. 1995. Overexpressison and localization of cathepsin B during the progression of human gliomas. *Clin Exp Metastasis*, 13, 49–56.
6. L. A. Liotta, et al. 1991. Tumor invasion and metastasis; an imbalance of positive and negative regulation. *Cancer Res.* 51, 5054s–59s.
7. R. Reich, et al. 1988. Effects of inhibitors of plasminogen activator, serine proteinases, and collagenase IV on the invasion of basement membranes by metastatic cells. *Cancer Res.* 48, 3307–12.
8. P. Mignatti, et al. 1993. Biology and biochemistry of proteinases in tumor invasion. *Physiol Rev.* 73, 161–95.
9. W. L. Monsky, et al. 1994. A potential marker protease of invasiveness, seprase, is localized on invadopodia of human malignant melanoma cells. *Cancer Res.* 54, 5702–10.
10. L. A. Liotta, et al. 1980. Metastatic potential correlates with enzymatic degradation of basement membrane collagen. *Nature*, 284, 67–8.
11. M. R. Emmert-Buck, et al. 1994. Increased gelatinase A (MMP-2) and cathepsin B activity in invasive tumor regions of human colon cancer samples. *Am J Pathol.* 145, 1285–90.
12. L. Ossowki, et al. 1983. Antibodies to plasminogen activator inhibit human tumor metastasis. *Cell*, 35, 611–19.
13. P. Mignatti, et al. 1986. Tumor invasion through the human amniotic membrane; requirement for a proteinase cascade. *Cell*, 47, 487–98.
14. C. F. Sier, et al. 1994. Inactive urokinase and increased levels of its inhibitor type 1 in colorectal cancer liver metastasis. *Gastroenterology*, 107, 1449–56.
15. B. F. Sloane, et al. 1981. Lysosomal cathepsin B: correlation with metastatic potential. *Science*, 212, 1151–3.
16. B. F. Sloane, et al. 1984. Cysteine proteinases and metastasis. *Cancer Metastasis Rev.* 3, 249–63.
17. E. Elliott, et al. 1996. The cysteine protease cathepsin B in cancer. *Perspect Drug Discov Design.* 6, 12–32.
18. T. T. Lah, et al. 1995. Cathepsins D, B and L in breast carcinoma and in transformed human breast epithelial cells (HBEC). *Biol Chem Hoppe-Seyler*, 376, 357–63.
19. P. B. Scaddan, et al. 1993. Characterization of cysteine proteases and their endogenous inhibitors in MCF-7 and adriamycin-resistant MCF-7 human breast cancer cells. *Inv Metastasis*, 13, 301–13.
20. R. A. Maciewicz, et al. 1989. Immunodetection of cathepsins B and L present in and secreted from human premalignant and malignant colorectal tumour cell lines. *Int J Cancer*, 43, 478–86.
21. F. Oian, et al. 1989. Expression of five cathepsins in murine melanomas of varying metastatic potential and normal tissues. *Cancer Res*, 49, 1870–5.
22. M. J. Murnane, et al. 1991. Stage-specific increases in cathepsin B messenger RNA content in human colorectal carcinoma. *Cancer Res*, 51, 1137–42.
23. T. Inoue, et al. 1994. Cathepsin B expression and laminin degradation as factors influencing prognosis of surgically treated patients with lung adenocarcinoma. *Cancer Res*, 54, 6133–6.
24. S. A. Rempel, et al. 1994. Cathepsin B expression and localization in glioma progression and invasion. *Cancer Res*, 54, 6027–31.
25. E. Campo, et al. 1994. Cathepsin B expression in colorectal carcinomas correlates with tumor progression shortened patient survival. *Am J Pathol*, 145, 301–9.
26. K. Sheahan, et al. 1989. Cysteine protease activities and tumor development in human colorectal carcinoma. *Cancer Res*, 49, 3809–14.
27. V. Evers, et al. 1985. The digestion of phagocytosed collagen is inhibited by the proteinase inhibitors leupeptin and E-64. *Collagen Rel Res*, 5, 315–36.
28. C. J. F. Van Noorden, et al. 1991. Selective inhibition of cysteine proteinases by Z-Phe-Ala-CH$_2$F suppresses digestion of collagen by fibroblasts and osteoclasts. *Biochem Biophys Res Commun*, 178, 178–84.
29. B. F. Sloane, et al. 1986. Cathepsin B: association with plasma membrane in metastatic tumors. *Proc Natl Acad Sci USA*, 83, 2483–7.
30. J. Rozhin, et al. 1994. Pericellular pH affects distribution and secretion of cathepsin B in malignant cells. *Cancer Res*, 54, 6517–25.
31. D. Keppler, et al. 1994. Secretion of cathepsin B and tumour invasion. *Biochem Soc Trans*, 22, 43–9.
32. V. Y. Reddy, et al. 1995. Pericellular mobilization of the tissue-destructive cysteine proteinases, cathpsins B,L, and S, by human monocyte-derived macrophages. *Proc Natl Acad Sci USA*, 92, 3849–53.
33. C. J. F. Van Noorden, et al. 1989. Localization and cytophotometric analysis of cathepsin B activity in unfixed and undecaclcified cryostat sections of whole rat knee joints. *J Histochem Cytochem*, 37, 617–24.
34. C. J. F. Van Noorden, et al. 1988. Cysteine proteinase activity in arthritic rat knee joints and the effects of a selective systemic inhibitor, Z-Phe-Ala-CH$_2$F. *J Rheumatol*, 15, 1525–35.
35. M. Erdel, et al. 1990. Localization of cathepsin B in two human lung cancer cell lines. *J Histochem Cytochem*, 38, 1313–21.

36. E. Spiess, et al. 1994. Cathepsin B activity in human lung tumor cell lines; ultrastructural localization, pH sensitivity, and inhibitor status at the cellular level. *J Histochem Cytochem*, 42, 917–29.

37. S. J. Chan, et al. 1986. Nucleotide and predicted amino acid sequences of cloned human and mouse preprocathepsin B cDNAs. *Proc Natl Acad Sci USA*, 83, 7721–5.

38. D. Keppler, et al. 1994. Latency of cathepsin B secreted by human colon carcinoma cells is not linked to secretion of cystatin C and is relieved by neutrophil elastase. *Biochem Biophys Acta*, 1226, 117–25.

39. C. B. Basbaum, et al. 1996. Focalized proteolysis—spatial and temporal regulation of extracellular matrix degradation at the cell surface. *Curr Opin Cell Biol*, 8, 731–8.

40. R. E. Essner, et al. 1994. Cysteine proteinase inhibitors decrease articular cartilage and bone destruction in chronic inflammatory arthritis. *Arth Rheum*, 37, 236–47.

41. G. Harth, et al. 1993. Peptide-fluoromethyl ketones arrest intracellular replication and intercellular transmission of *Trypanosomacruzi*. *Mol Biochem Parasitol*, 58, 17–24.

42. C. C. Calkins, et al. 1995. Mammalian cysteine protease inhibitors; biochemical properties and possible roles in tumor progression. *Biol Chem Hoppe-Seyler*, 376, 71–80.

43. J. S. Mort, et al. 1986. Interrelationship of active and latent secreted human cathepsin B precursors. *Biochem J*, 233, 57–63.

44. R. L. Marquet, et al 1984. Interferon treatment of a transplantable rat colon adenocarcinoma; importance of tumor site. *Int J Cancer*, 33, 689–92.

45. K. P. Dingemans, et al. 1994. Developmental stages in experimental liver metastases; relation to invasiveness. *Int J Cancer*, 57, 433–9.

46. P. Griffini, et al. 1997. Three-dimensional reconstruction of colon carcinoma metastases in liver. *J Microsc*, 187, 12–21.

47. L. H. P. Caro, et al. 1988. 3-Methyladenine, an inhibitor of autophagy, has multiple effects on metabolism. *Eur J Biochem*, 175, 325–9.

48. C. J. F. Van Noorden, et al. 1997. Ala-Pro-cresyl violet, a synthetic fluorogenic substrate for the analysis of kinetic parameters of dipeptidyl peptidase IV (CD26) in individual living rat hepatocytes. *Anal Biochem*, in press.

49. A. Jonker, et al, 1995. Image analysis and image processing as tools to measure initial rates of enzyme reactions in sections: distribution patterns of glutamate dehydrogenase activity in rat liver lobules. *J Histochem Cytochem*, 43, 1027–34.

50. R. E. Wilson, et al. 1989. Enhanced synthesis of specific proteins, RNA, and DNA caused by hypoxia and reoxygenation. Int *J Radiat Oncol*, 16, 957–61.

51. S. M. Smorenburg, et al. 1996. Alpha2-macroglobulin is mainly produced by cancer cells and not by hepatocytes in rats with colon carcinoma metastases in liver. *Hepatology*, 23, 560–70.

52. P. Griffini, et al. 1996. Kupffer cells and pit cells are not effective in the defense against experimentally induced colon carcinoma metastasis in rat liver. *Clin Exp Metastasis*, 14, 367–80.

53. N. K. Ahmed, et al. 1993. peptidyl fluoromethyl ketones as inhibitors of cathepsin B. *Biochem Pharmacol*, 44, 1201–7.

54. C. J. F. Van Noorden, et al. 1992. *Enzyme Histochemistry. A Laboratory Manual of Current Methods, Oxford:* BIOS.

55. J. Caldero, et al. 1989. Lectin-binding sites in neoplastic and non-neoplastic colonic mucosa of 1,2-dimethyldrazine-treated rats. *Lab Invest*, 61, 670–6.

56. S. W. Cox, et al. 1987. Preliminary studies on cysteine and serine proteinase activities in inflamed human gingiva using different 7-amino-4-trifluoromethyl coumarin substrates and protease inhibitors. *Arch Oral Biol*, 32, 599–605.

57. M. Pagano, et al. 1986. Inhibition of the cathepsin B like proteinase by a low molecular weight cysteine-proteinase inhibitor from ascitic fluid and plasma alpha 2 macroglobulin. *Biochem Cell Biol*, 64, 1218–25.

58. S. Yagel, et al. 1989. Suppression by cathepsin L inhibitors of the invasion of amnion membranes by murine cancer cells. *Cancer Res*, 49, 3553–7.

59. S. M. Redwood, et al. 1992. Abrogation of the invasion of human bladder tumor cells by using protease inhibitor(s). *Cancer*, 69, 1212–19.

60. R. Navab, et al. 1997. Inhibition of carcinoma cell invasion and liver metastases formation by the cysteine proteinase inhibitor E-64. *Clin Exp Metastasis*, 15, 121–9.

61. I. J. Fidler, 1991. Cancer metastasis. *Br Med Bull*, 47, 157–77.

62. I. J. Fidler, et al. 1994. Modulation of tumor cell response to chemotherapy by the organ environment. *Cancer Metastasis Rev*, 13, 209–22.

63. M. Nakajima, et al. 1990. Influence of organ environment on extracellular matrix degradative activity and metastasis of human colon carcinoma cells. *J Natl Cancer Inst*, 82, 1890–8.

64. A. M. Wheatley, et al. 1993. Interpretation of the laser Doppler flow signal from the liver of the rat. *Microvasc Res*, 45, 290–301.

65. F. C. Richardson, et al. 1988. Hepatocyte initiation during continuous administration of diethylnitrosamine and 1,2-sym-dimethylhydrazine. *Cancer Res*, 48, 988–92.

66. L. W. Elmore, 1991. Phenotypic characterization of metaplastic intestinal glands and ductular hepatocyates in cholangiofibrotic lesions rapidly induced in the caudate liver lobe of rats treated with furan. *Cancer Res*, 51, 5752–9.

67. H. B. Jones, et al. 1993. Phenobarbital-induced hepatocellular proliferation: anti-bromodeoxyuridine and anti-proliferating cell nuclear antigen immunocytochemistry. *J Histochem Cytochem*, 41, 21–7.

68. Y. Shirai, et al. 1996. Colorectal caracinoma metastases to the liver —does primary tumor location affect its lobar distribution. *Cancer*, 77, 2213–16.

69. W. J. Dodds, et al. 1990. Caudate lobe of the liver: anatomy, embryology, and pathology. *Am J Roentgenol*, 154, 87–93.

70. E. Barbera-Guillem, et al. 1989. Selective implantation and growth in rats and mice of experimental liver metastasis in acinar zone one. *Cancer Res*, 49, 4003–10.

71. E. Barbera-Guillem, et al. 1991. Differences in the lectin-binding patterns of the periportal and perivenous endothelial domains in the liver sinusoids. *Hepatology*, 14, 131–9.

72. C. D. Dijkstra, et al. 1985. The heterogeneity of mononuclear phagocytes in lymphoid organs: distinct macarophage subpopulations in the rat recognized by monoclonal antibodies ED1, ED2 and ED3. *Immunology*, 54, 589–99.

73. W. R. McMaster, et al. 1979. Identification of la glycoproteins in rat thymus and purification from rat spleen. *Eur J Immunol*, 9, 426–33.

74. L. Bouwens, et al. 1992. Pit cells in the liver. *Liver*, 12, 3–9.

75. A. M. Duijvestijn, et al. 1992. Antibodies defining rat endothelial cells: RECA-1. A pan-endothelial cell-specific monoclonal antibody. *Lab Invest*, 66, 459–66.

76. A. P. Robinson, et al. 1986. MRC OX43: a monoclonal antibody which reacts with all vascular endothelium in the rat except that of brain capillaries. *Immunology*, 57, 231–7.

77. E. N. Lamme, et al. 1996. Extracellular matrix characterization during healing of full-thickness wounds treated with a collagen/elastin dermal substitute shows improved skin regeneration in pigs. *J Histochem Cytochem,* 44, 1311–22.

78. L. Christensen, 1990. Fibronectin: a discrimination marker between small invasive carcinomas and benign proliferative lesions of the breast. *Apmis,* 98, 615–23.

79. M. V. Gulubova, 1996. Ultrastructural sinusoidal changes in extrahepatic cholestasis—light and electron microscopic immunohistochemical localization of collagen type III and type IV. *Acta Histochem,* 98, 271–83.

80. V. Everts, et al. 1994. Type VI collagen is phagocytosed by fibroblasts and digested in the lysosomal apparatus: involvement of collagenase, serine proteinases and lysosomal enzymes. *Matrix Biol,* 14, 665–76.

Proteolysis is a key multistep process in the invasion of host tissue by cancer cells during tumor progression (1 to 9). (The references are listed above.) Histopathological studies and in vitro studies of cultured cancer cells with metastatic potential have revealed that matrix metalloprotenases (7,9, 10,11), plasminogen activators (7,12,13,14) and cathepsins (11 and 15 to 24) are involved.

Sloane and co-workers earlier proposed that the presence of cathepsin B either at the plasma membrane of cancer cells or in the extracellular space around cancer cells is significant for metastasis (11,15,16,17 and 25). Cathepsin B, the most prominent representative of the cysteine proteinase subclass (26), is normally present in the lyposomes where it is involved in breakdown of proteins after phagocytosis or autophagy. When cathepsin B is blocked, lysosomal protein breakdown is signifcantly curtailed (27,28). Under certain conditions, cathepsin B is not sorted to the lysosomes but secreted (29,30,31), for example by macrophages during chronic inflammation (32) and by chondrocytes during the acute phase of arthritis (33,34). Secretion and association of cathepsin B with the plasma membrane have been found in metastatic cancer cells but not in cancer cells lacking this potential (30,35,36). It is dependent on a functionally intact microtubular network (30,31) and can be induced by acidification of the extracellular micro-environment (30).

REFERENCES CONCERNING AMINO ACID CRESYL VIOLET

1A. G. N. Jonges, et al., (1992) J. Biol. Chem. 267, 4878–4881.

2A. C. J. F. Van Noorden, et al., (1995) Histochem. J. 27, 101–118.

3A. C. J. F. Van Noorden, et al., (1995) Histochem. Cell Biol. 103, 93–101.

4A. A. Jonker, et al., (1996) Histochem. Cell Biol. 106, 437–443.

5A. Y. Nakae et al., (1994) Histochem. J. 26, 292–297.

6A. Y. Nakae et al., (1995) Histol. Histopathol. 10, 463–479.

7A. V. Everts et al., (1985) Collagen Rel. Res. 5, 315–336.

8A. V. Everts, et al., (1992) J. Cell. Physiol 150, 221–231.

9A. C. J. F. Van Noorden et al., (1991) Biochem. Biophys. Res. Comm. 178, 178–184.

10A. R. E. Smith, et al., (1992) Histochem. J. 24, 637–647.

11A. C. J. F. Van Noorden, et al., (1988) J. Rheumatol. 15, 1525–1535.

12A. R. E. Esser, et al., (1994) Arthrit. Rheum. 37, 236–247.

13A. C. J. F. Van Noorden, et al., (1996) Acta Histochem. Cytochem. suppl. I, 126–127.

14A. S. M. Smorenburg. et al., (1996) Hepatology 23, 560–570.

15A. M. J. Scanlan et al., (1994) Proc. Natl. Acad. Sci. USA 91, 5657–5661.

16A. W. Scholz et al., (1985) Cell Immunol. 93, 199–211.

17A. P. Ruiz, et al., (1996) Cytometry 23, 322–329.

18A. G. Trugnan, et al., (1995) in Dipeptidyl Peptidase IV (CD26) in Metabolism and the Immune Response (Fleischer, B., Ed.), pp. 79–98, Springer, N.Y.

19A. M. Brandsch, et al., (1995) in Dipeptidyl Peptidase IV (CD26) in Metabolism and the Immune Response (Fleischer, B., Ed.), pp. 111–129, Springer, N.Y.

20A. R. Gossrau, (1981) J. Histochem. Cytochem. 29, 464–480.

21A. T. Tanaka, et al., (1992) J. Immunol. 149, 481–486.

22A. T. Tanaka, et al., (1994) Proc. Natl. Acad. Sci. USA 91, 3082–3086.

23A. P. Naquet, et al., (1989) Immunol. Rev. 111, 177–193.

24A. N. H. Dang, et al., (1990) J. Exp. Med. 172, 649–652.

25A. Y. Shimizu, et al., (1991) FASEB J. 5, 2292–2299.

26A. W. Reutter, et al., (1995) in Dipeptidyl Peptidase IV (CD26) in Metabolism and the Immune Response (Fleischer, B., Ed.), pp. 55–78, Springer, N.Y.

27A. C. Callebaut, et al., (1993) Science 262, 2045–2050.

28A. R. E. Smith, et al., (1997) AIDS Res. Hum. Retrov. in press.

29A. T. Kubota, et al., (1992) Clin. Exp. Immunol. 89, 192–197.

30A. L. H. P. Caro, et al., (1988) Eur. J. Biochem. 175, 325–329.

31A. U. Neumann, et al., (1991) J. Enzyme Inh. 4, 213–226.

32A. B. Boduszek, et al., (1994) J. Med. Chem. 37, 3969–3976.

33A. A. Jonker, et al., (1995) J. Histochem. Cytochem. 43, 1027–1034.

34A. T. Wilson, (1989) in The Handbook of Confocal Microscopy (Pawley, J., Ed.), pp. 113–126, IMR Press, Madison Wis.

35A. A. Jonker, et al., (1997) Histochem J. 29, 347–364.

36A. F. W. D. Rost, (1991) Quantitative Fluorescence Mircoscopy, Cambridge University Press, Cambridge.

37A. S. P. Leytus, et al., (1983) Biochem. J. 215, 253–260.

38A. S. P. Leytus, et al., (1983) Biochem J. 209, 299–307.

39A. I. Assfalg-Machleidt, et al., (1992) Biol. Chem. Hoppe-Seyler 373, 433–440.

40A. B. Ulbricht, et al., (1995) Biol. Chem. Hoppe-Seyler 376, 407–414.

41A. J. M. Petit, et al., (1993) Biol. Cell. 78, 1–13.

42A. G. Rothe, et al., (1992) Biol. Chem. Hoppe-Seyler 373, 547–554.

43A. S. Ganesh, et al., (1995) Cytometry 20, 334–340.

44A. W. J. McGrath, et al., (1996) Virology 217, 131–138.

45A. C. J. F. Noorden, et al., (1997) Clin. Exp. Metast. in press.

BACKGROUND CONCERNING DIPEPTIDYL PEPTIDASE IV

Quantitative enzyme histochemical methods have been applied to determine kinetic parameters of enzymes in intact unfixed tissue sections to obtain information on behaviour of enzymes in their own cellular environment and zonal differences in their function within a tissue (see references 1A–6A) (References are immediately above). These studies demonstrated that both variations and regional differences in the kinetic parameters of several enzymes occur which partly explain the enormous plasticity of tissues to adapt to alterations in the environment. Although unfixed cryostat sections is one step closer to the in vivo situation than homogenates, they still do not provide information on how enzymes behave in vivo. We want to establish the exact role of proteases in physiological and pathophysiological processes. Examples are turnover of collagen (7A–9A), activation of the immune system (10A), arthritis (11A,12A) and metastasis of cancer (13A,14A). For such studies, methods to measure protease reactions in individual living cells are needed. To visualize protease activity in single cells, a new class of fluorogenic substrates for proteases containing cresyl violet was synthesized. This is a highly fluorescent leaving group after proteolytic cleavage of the amide bonds.

Dipeptidyl peptidase IV (DPPIV) is an ectopeptidase present at the plasma membrane of many cell types. It is a transmembrane glycoprotein with a short cytoplasmic tail, one hydrophobic transmembrane segment and a large extracellular domain (15A). DPPIV is involved in activation of bioactive molecules such as cytokines (16A,17A) and it participates in the extracellular digestion of polypeptides to provide substrates for peptide and amino acid reabsorption (18A,19A). In hepatocytes, the enzyme is present at the apical bile canalicular membrane and exerts its function in the lumen of bile canaliculi (20A). DPPIV is homologous with CD26 (21A,22A) which has a receptor function for T cell activation and can bind to collagen (23A–26A). The CD26 molecule can become heavily glycosylated and sialylated and this regulates its receptor function strongly. For example, it is involved in several immune-mediated diseases, including AIDS. It can act as a binding protein for HIV (27A) but only when it is heavily sialylated (28A). Inhibition of DPPIV activity by specific tripeptides has an immuno suppressive effect in vivo (29A).

Amino acid synthesis and coupling reaction technology of the art includes but is not limited to U.S. Pat. Nos. 3,886,132; 4,318,905; 4,587,046; 4,771,124; 4,837,305; 5,134,232; 5,527,882, 5,602,288 and 5,637,759, all of which are incorporated herein by reference in their entirety.

All patents, references, articles, publications, standards and the like are incorporated herein by reference in their entirety.

As can be seen from the above background, a need exists to be able to determine easily the presence of an active enzyme in a cell or tissue. The present invention provides such a detection method and a kit for easy use.

SUMMARY OF THE INVENTION

The present inventions concern fluorogenic substrates for an enzyme (i.e. a protease) based on the leaving group cresyl violet, including, but not limited to:

A method to detect the presence of an enzyme in in vivo or in vitro cell or tissue, which method comprises:
 (a) obtaining a cell or tissue sample to be analyzed;
 (b) contacting the cell or tissue sample with a substrate of the structure selected from the group consisting of:

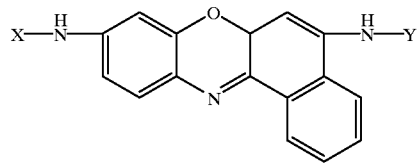

X=H or one or more natural or synthetic amino acids with or without amino blocking groups,
Y=H or one or more natural or synthetic amino acids with or without amino blocking groups,
wherein X and Y are the same or different and are amino acid sequences of between about 1 to 1,000,000 amino acids wherein each amino acid is the same or a different amino acid, with the proviso that at least one of X or Y is at least one amino acid;
 (c) or added to cell culture;
 (d) when an enzyme is present in the tissue sample which degrades X, Y and combinations thereof, fluorescent cresyl violet where X and Y are H is released in the tissue sample;
 (e) detecting the presence and amount of the enzyme present by the detection and quantification of the fluorescence produced; and
 (f) optionally comparing the fluorescence to a pre-calibrated fluorescence scale to quantify the fluorescence present.

Preferably, the amino acid sequences are between about 1 and 100,000, more preferably between about 1 and 10,000, between about 1 and 1,000 or between about 1 and 10. In specific aspects the amino acid sequences are between about at least 2 to 1,000,000, between at least 2 and 100,000; between at least 2 and 10,000 between at least 2 and 1,000 amino acids or between 2 and 10 amino acids.

A diagnostic kit to determine the presence of an enzyme in tissue or culture, which kit comprises:
 (1) a substrate of the structure selected from the group consisting of:

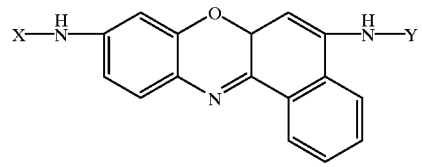

X=H or one or more natural or synthetic amino acids with or without amino blocking groups,
Y=H or one or more natural or synthetic amino acids with or without amino blocking groups,
wherein X, Y, and combinations thereof, with the proviso that at least one of X or Y is at least one amino acid, which are degraded in the presence of an enzyme to release fluorescent cresyl violet which is detected and quantified.

The method or kit wherein the enzyme is a protease.
The method or kit wherein X=Y=alanyl-proline or Z-arg.
The method or kit wherein X=Y or X does not equal Y, and X having of 1 to 1000 amino acids and Y having 1 to 1000 amino acids are each independently selected from synthetic amino acids or natural amino acids such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Preferably X and Y are between 1 and 10 amino acids.

A method to produce a substrate of the structure:

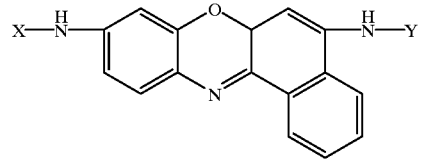

X=H or one or more natural or synthetic amino acids with or without amino blocking groups, Y=H or one or more natural or synthetic amino acids with or without amino blocking groups, with the proviso that at least one of X or Y is at least one amino acid, which method comprises:

(a) obtaining a protected amino acid sequence of interest;

(b) reacting the amino acid sequence with an amino acid coupling agent;

(c) suspending the coupled product of step (b) in a dipolar aprotic solvent which contains a strong organic base at between about −20° C. and +20° C., and adding additional, same or different coupling agent;

(d) contacting the product of step (c) with cresyl violet hydrochloride at between about −20° C. and +20° C. with mixing for between about 10 and 30 hours at between about −20° C. and +20° C.;

(e) removing dipolar aprotic solvent, strong organic base solvent, and other materials generated in the reaction under vacuum up to about +60° C.;

(f) dissolving the product of step (e) in dipolar aprotic crystallization solvent;

(g) purifying the liquid product of step (f) by washing one or more times with aqueous acid, aqueous saturated brine, aqueous saturated bicarbonate and water;

(h) drying the dipolar aprotic solvent of step (g) using a solid drying agent;

(i) separating the solid drying agent and removing from the liquid the solvent of step (h) to produce the amino acid coupled—cresyl violet; and (j) optionally further purifying the amino acid coupled—cresyl violet.

Dipolar aprotic solvent refers to those conventional solvents which do not have one or more active hydrogens, e.g., dimethylformamide, diethylacetamide, dimethlysulfoxide, benzene, chlorobenzene, toluene, chloroform, and the like. Combinations of solvents are included.

Dipolar aprotic crystallization solvent includes those generally low boiling organic substances which are generally used without an active proton, e.g., esters such as ethyl acetate, ethers, cyclic ethers, ketones, chlorinated hydrocarbons, and the like. Combinations of solvents are included.

Strong organic base includes, for example, pepidine, pyrrole substituted pyridine, substituted pyrrole, dialkylamine, trialkylamine, where alkyl is $C_1$ to $C_6$ carbons, and the like. Combinations of strong bases are included.

The method described above wherein the amino acid sequences are independently selected from the group consisting of Ala-pro, A-Arg-, A-Asp-glu-val-asp-, (SEQ. ID NO: 1); A-ile-glu-thr-asp-, (SEQ. ID NO: 2); A-Tyr-Val-Ala-Asp-, (SEQ. ID NO: 3); A-Trp-Glu-His-Asp-, (SEQ. ID NO: 4); A-Val-Asp-Val-Ala-Asp-, (SEQ. ID NO: 5); A-Val-Asp-Glu-Gln-Asp-, (SEQ. ID. NO: 6); A-Asp-Glu-Val-Asp-, (SEQ. ID NO: 7); A-Leu-Glu-Val-Asp-, (SEQ. ID NO: 8); A-Trp-Glu-His-Asp-, (SEQ. ID NO: 9); A-Val-Glu-Ile-Asp-, (SEQ. ID NO: 10); A-Val-Gln-Val-Asp-, (SEQ. ID NO: 11); A-Asp-Glu-Val-Asp-, (SEQ. ID NO: 12); A-Ile-Glu-Thr-Asp-, (SEQ. ID NO: 13); A-Leu-Glu-Val-Asp-, (SEQ. ID NO: 14); A-Asp-Glu-Val-Asp-, (SEQ. ID NO: 15); A-Val-Ala-Asp; and A-Ile-Glu-Pro-Asp-, (SEQ. ID NO: 16), wherein A-CBZ or Ac, wherein A- is carbobenzoxy or acetyl.

This invention is also useful to detect caspases, that is, enzymes involved in apoptosis (aka programmed cell death). Amino acid groups X and Y include (X-asp-glu-val-asp-) (SEQ. ID NO: 1) a substitute for apopane or caspase 3 or (x-ile-glu-thr-asp)(SEQ. ID NO: 2), a substrate for FLICE or caspase-8, wherein X is an amine blocking group such as CBZ (carbobenzoxy) or Ac (acetyl). The amino acid sequences have been shown in the art to be useful for the other fluorogenic detecting groups and are useful wherein cresyl violet is the fluorogenic group.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 1 shows the reaction scheme for producing cresyl violet from (Alo-Pro)$^2$ cresyl violet in the presence of DPPIV.

FIG. 2A shows the relationship between fluorescence and concentration of cresyl violet.

FIG. 2B shows the relationship between fluorescence and incubation time.

FIG. 3 shows cresyl violet generated in living rat hepatocytes.

FIG. 4A shows the formation of cresyl violet fluorescence in a single hepatocytes as a function of time in the presence and absence of Ala-Pro-cresyl violet in suspensions of hepatocytes as measured by fluorometry.

FIG. 4B shows the formation of cresyl violet fluorescence is function of time in the presence and absence of Ala-Pro-cresyl violet in suspensions of hepatocytes as measured by fluorometry.

FIG. 4C shows the formation of cresyl violet fluorescence or a function of time in the presence and absence of Ala-Pro-cresyl violet in membrane fractions as measured by fluorometry.

FIG. 5 shows the relationship between initial velocity of DPPIV in living hepatocytes and the Ala-Pro-cresyl violet concentration.

FIG. 6 shows characteristics on inhibition of DPPIV activity by Ala-Pip$^p$ (OPh-4C1)$_2$.

FIG. 7 shows the inverse relationship between $K_m$ and $V_{max}$ in DPPVI in living hepatocytes.

FIG. 8A shows flow cylometric analysis of DPPIV activity in individual hepatocytes using Ala-Pro-cresyl violet as substrate (fluorescence vs forward scatter).

FIG. 8B shows a selection of hepatocytes from FIG. 8A showing generation of fluorescence of cresyl violet as function of time.

FIGS. 9A,9B,9C,9D, and 9E show cathepsin B expression in rat colon cancer cells (CC531) under various conditions.

FIG. 10 shows a photomicrograph of a cryostat section of rat liver containing CC531 colon cancer colonies.

DETAILED DESCRIPTION OF THE INVENTION AND PREFERRED EMBODIMENTS

Discussion Concerning Cathepsin B

Definitions:

As used herein:

"Blocked amino acids" refers to the terminal amine of an amino acid or a polypeptide with a conventional blocking group. Preferably the blocking group is carbobenzoxy (CBZ) or acetyl (Ac).

"in vivo" refers to the conventional definition of a living cell and this cell may be in a mammal or in a living cell culture.

"Tissue" or "cell" refers to any "tissue or cell" from a mammal. Liver tissue or cells are described herein as examples only. The invention is not to be restricted to liver tissue or cells, and can be any tissue or cell.

The advantages of an amino acid substituted cresyl violet substrate include but are not limited to:

1. These substrates fluorescence only in the presence of the corresponding enzyme. In the absence of the enzyme no fluorescence is detected. 2. The free cresyl violet is excited with conventional green light which light is harmless to the cell or the tissue.

3. The free cresyl violet is sufficiently water soluble to avoid accumulation around the mitochondrea of the cell.

4. The amino acid cresyl violet substrates are proven to penetrate the cell membrane and function in living cells.

The extracellular action of cathepsin B is an early step in the proteolytic cascade involved in metastasis by activation of proforms of plasminogen activators and matrix metalloproteinases that are present in the extracellular space. Proteases are synthesized in an inactive proform or preproform and need to be activated for example by cleavage by other proteases before they are able to degrade proteins (37,38, 39). Therefore, the role of cathepsin B in an in vivo rat model of colon cancer metastasis in the liver was established. Metastasis was mimicked by administration of rat colon cancer cells in the portal vein of rats. We tested whether development of metastases could be inhibited by treatment of the animals with a selective non-toxic water-soluble small molecular inhibitor of cathepsin B, Mu-Phe-homoPhe-fluoro-methylketone (FMK) (40,41). First, the localization of cathepsin B and its activity at the plasma membrane of the cancer cells was investigated. For this purpose, a new synthetic fluorogenic substrate for cathepsin B, [Z-Arg]$^2$-cresyl violet was developed, which permits the localization of its activity in living cells with the use of confocal scanning laser microscopy (CSLM). The use of living cells was considered to be of vital importance because activity of proteases in vivo is determined by activation of the proforms, suppression by endogeneous inhibitors (6,30, 42) and the cellular microenvironment of the enzyme (39). This is particularly relevant for cathpsin B which normally functions at acidic pH in the lysosomes, whereas the extracellular pH is slightly alkaline (43).

The present invention reveals for the first time that cathepsin B which is localized at the plasma membrane of cancer cells with potential to metastasize is active. FMK inhibited only extracellular and not intracellular cathepsin B activity apparently because it had not been taken up by the living cells. This phenomenon was also observed when living malaria parasites were incubated with the same compound (41). It clearly demonstrates that compounds can be designed to selectively inhibit enzymes on the cell surface without perturbation of that enzyme in the cytoplasm or organelles such as the lysosomes. In contrast, the substrate was rapidly available for intracellular proteolytic cleavage because it is much more lipophilic than the inhibitor. These findings that cathepsin B is present at the plasma membrane of the CC531 cancer cells is in agreement with other immunocytochemical studies (35,36). However, unlike our newly developed enzyme cytochemical method to localize activity in living cells, immunocytochemical methods cannot discriminate between active and inactive cathepsin B in its (pre)proform or complexed with its natural inhibitors such as cystatins, stefins or α2-macroglobulin (8,36,57).

In the second part of this invention, it was demonstrated that in vivo treatment of rats with the selective cathepsin B inhibitor, FMK, affected growth of CC531 cancer cells in the liver in the three major lobes of the liver. Thus, in vivo treatment with the inhibitor not only affects early events in invasion and/or survival of cancer cells, but also inhibits growth of metastases in the larger lobes of the liver which comprise 90% of the liver. The observations that invasion and growth of cancer cells can be blocked in vitro and in vivo by inhibitors of cathepsin B (58–60) and that decreased activity of cysteine proteinase inhibitors is correlated with malignancy (42) are supported by our in vivo evidence that cathepsin B plays a significant role in liver colonization. In contrast, this quantitative analysis demonstrates that the caudate lobe provides a more beneficial environment for invasion and growth of cancer cells than the large lobes whereas inhibition of cathepsin B does not reduce number or size of metastases in the former lobe. Although the caudate lobe comprises only 10% of the total liver volume in rats and human, it is apparently a relatively large risk factor for developing metastases. It is well known that the microenvironment in organs influences the outcome of metastasis (61–63), but as far as we know this is the first report of intraorgan heterogeneity with respect to metastasis.

Rheological aspects cannot explain this difference between the caudate lobe and other lobes. When spherical beads with the size of cancer cells were administered into the vena portae, similar numbers of beads were found in all liver lobes (64). Chemical induction of hepatocellular proliferation, carcinogenesis and cholangiofibrosis can also lead to a lobe-dependent heterogeneous response (65–67). We have not been able to find a cause for the interlobar heterogeneity of tumor development which also occurs in humans (68). There was no difference in cathepsin B activity or in the effect of in vivo treatment with FMK on cathepsin B activity in the four lobes. In all lobes, activity was similar and inhibited by apparox. 50% by FMK treatment. Furthermore, no differences were found in the host defense against cancer cells in the four lobes on the basis of the number and activation state of immunocompetent cells. Distribution patterns of major extracellular matrix components and adhesion molecules were also comparable in the four lobes.

The preference of colon cancer to grow in the caudate lobe can be related to its different embryonic and postnatal development (68,69). It gives this small lobe comparatively better oxygenation than the other lobes due to a different vascularization and probably a different make up of the endothelial cell compartment. The endothelial cell compartment is heterogeneous in the liver and this phenomenon has been linked with selectivity of implantation of metastases at certain sites (70,71). Distinct differences between endothelial cell populations in the different liver lobes has not yet been demonstrated. It is unlikely that differences in size and thus in surface/volume ratio of the lobes play a significant role. At 7 days after inoculation of the cancer cells, tumors are found randomly distributed throughout the lobes. Only in later stages, tumors grow towards the liver capsule (45,46).

The different effects of in vivo treatment with a cathepsin B inhibitor in the lobes must be a consequence of one or more function(s) of cathepsin B and particularly of those of the plasma membrane-bound fraction of the enzyme in these processes. Cathepsin B can activate extracellular proteases, cleave compounds of the extracellular matrix or act as an adhesion molecule during invasion. The latter function would agree well with the affinity of the active site of the enzyme for a relatively large number of amino acid sequences and the relatively low activity of this lysosomal enzyme at extracellular neutral or slightly alkaline pH. On the other hand, our CSLM images of proteolytic activity against the cathepsin B substrate clearly show for the first time that this protease is functionally active in lysosomes of living normal cells and cancer cells and additionally at the plasma membrane of living colon cancer cells in the slightly alkaline culture medium. The latter activity was inhibited by the compound that was used for in vivo treatment (see FIG. 9).

Cancer Cells and Treatment of the Rats

An established rat colon carcinoma cell line, CC531, was used for all experiments. The parental cell line was obtained from a 1,2-dimethylhydrazine-induced moderately differentiated and weakly immunogenic colon adenocarcinoma in WAG-Rij rats (44). Cells were cultured in vitro at 37° C. as monolayers in Dulbecco's modification of Eagle's medium (ICN Biomedicals, Irvine, Ayrshire, UK) supplemented with 10% (w/v) fetal bovine serum, 2 mM glutamine, 100 IU penicillin/ml and 100 µg streptomycin/ml. Cells were washed in PBS and, after detachment by scraping and centrifugation (250 g, room temperature, 10 min), a single cell suspension at a final concentration of $1 \times 10^6$ cancer cells in 50 µl of PBS was obtained with a viability of at least 95% (45,46). Cell suspension were either used for cytochemical purposes or for in vivo administration to induce metastases in the liver.

Cytochemistry of CC531 Cells

For immunolocalization of cathepsin B, CC531 cell suspensions were diluted 20-fold in PBS. Cytospin preparations were made (250 g, room temperature, 10 min) and fixed in acetone at 4° C. for 7 min. Immunolocalization was performed with a polyclonal sheep antibody against human cathepsin B (Biogenesis. Poole, UK; 1:100 in PBS containing 0.2% (w/v) BSA). Incubations were performed at room temperature for 60 min in a moist dark chamber. A secondary donkey anti-sheep antibody conjugated with FITC (Sigma, St. Louis, Mo.: 1:250 in PBS containing 0.2% (w/v) BSA) was used after rinsing the preparations three times. Incubations lasted 60 min at room temperature in a moist dark chamber. After rinsing the preparations three times, they were mounted in anti-fading medium (Vectashield, Vector Labs, Burlingame, Calif.) and photographed using a fluorescence microscope (Orthoplan, Leica Wetzlar, Germany) and a NPL Fluotar oil-immersion objective (×50, NA 1.00). Excitation of FITC was performed at a wavelength of 385–425 nm and fluorescencee emission was captured at wavelengths greater than 460 nm. Controls were performed by replacing the first antibody by non-immune sheep serum in the same dilution.

Cathepsin B activity was detected in real-time in living CC531 cells and freshly prepared living rat hepatocytes after isolation by collagenase perfusion of livers of male mature rats after 24 h of starvation (47). At time point zero, cell preparations were diluted 20-fold in PBS containing either 10 µM $(Z-Arg)^2$-cresyl violet (Enzyme Systems Products, Dublin, Calif.) as fluorogenic substrate for cathepsin B (48) or 10 µM substrate and 20 µM FMK (Protek, Dublin, Calif.), as selective cathepsin B inhibitor (40,41). The fluorogenic substrate is not fluorescent but after proteolytic cleavage, liberated cresyl violet is fluorescent. Synthesis of the substrate is described elsewhere in Ref. 48. The substrate was dissolved first in dimethyl formamide (final concentration in the incubation medium was 1% (v/v)). An aliquot of 100 µl of the cell suspensions was brought into a well formed by a stainless steel ring attached to a glass slide (49). Images of cells were captured in real-time with a Leica CSLM fitted to a Leica Fluovert inverted microscopic equipped with a PL APO oil-immersion objective (×63, NA 1.40). Excitation was performed at a wavelength of 560 nm and fluorescence was captured at greater than 580 nm. Excitation with the use of green light is harmless to living cells. The pinhole aperture was set at 100 giving an optimized image (50). With fixed pinhole, filter combination and a laser power setting adjusted to give minimal fading, the photomultiplier gain and photometric offset were optimized. Cells were subjected to optical serial sectioning after each 60 s of incubation up to 300 s. Images in the X-Y plane were recorded with intervals of 0.5 µm in the Z direction. For analysis, each optical section was averaged eight times. Images were recorded in a 512×512 pixel format. The size of each pixel represented 0.015 µm² in the object. Confocal data stacks of 20–30 optical sections were processed with a 3D visualization computer program AVS (Advanced Visual Systems, Waltham, Mass.).

Induction of Metastasis in Rat Liver

Colon carcinoma tumors were induced in rat liver by injection of a single cell suspension containing $1 \times 10^6$ CC531 cells into the portal vein of 32 mature male WAG-Rij rats, weighing 180–200 g (Broekman, Someren, The Netherlands) as described previously in detail (46,51,52).

Treatment of Rats with FMK

Sixteen rats were treated orally with 20 mg FMK per kg body weight dissolved in PBS and 5% dimethylformamide daily for 14 days starting one week before administration of the CC531 cells and continuing until sacrifice. Oral administration was performed directly into the stomach with a plastic tube attached to a syringe. Dosage and type of treatment were selected on the basis of previous experiments in which rats were treated with FMK-related inhibitors of cathepsins (34,40,53). The other 16 animals were treated similarly with PBS and dimethylformamide only. The $LD_{50}$ of this type of FMK is at least 20-fold higher than the dosages used in the present experiment (40,53).

Preparation of Cryostat Sections of Liver

Seven days after administration of CC531 cells, the animals were weighed and sacrificed with an overdose of sodium pentobarbital. Livers were removed immediately, the individual lobes were weighed and dissected and cut into small pieces (up to 5 mm thick) according to a rigid dissection scheme. The left lateral lobe was cut into eight pieces, the median lobe into nine pieces, the right lateral and caudate lobes into four pieces. Tissue fragments were frozen in liquid nitrogen and the material was kept at −80° C. until further use. Twenty-one sites were randomly selected in all lobes of each liver before the experiments were carried out. From these sites, sections (8 µm thick) were cut on a motor-driven cryostat with a rotary retracting microtome (Bright, Huntingdon, UK) at a constant but low speed and a cabinet temperature of −25° C. Sections were picked up onto clean glass slides and stored in the cryostat cabinet until used. These methods have been described in detail in Reference 54.

Staining of Tissue Sections

To facilitate recognition of cancer cells, cryostat sections were stained either with the periodic acid Schiff (PAS) reaction (54) or immunohistochemically using the lectin Ulex europaeus agglutinin I (Dako, Glostrup, Denmark), a selective marker of CC531 cells in rat (51,55). Immunocompetenet cells, endothelial cells and components of the extracellular matrix were localized with a panel of antibodies (Table 1) as described in detail by Griffini et al. (52).

Control incubations were performed by replacing the first antibodies by non-immune sera in the same dilutions.

TABLE 1

Table 1. Antibodies used for the immunohistochemical demonstration of immunocompet cells, endothelial cells and components of the extracellular matrix in rat livers containing colon cancers.

| Antibody | Specificity | Type of Antibody | Reference |
|---|---|---|---|
| ED2 (Serotec, Oxford, UK) | Kupffer cells | Mouse monoclonal | (72) |
| ED1 (Serotec) | Macrophages | Mouse monoclonal | (72) |
| OX3 (Serotec) | Activated immuno-competent cells | Mouse monoclonal | (73) |
| OX8 (Serotec) | Lymphocytes, pit cells | Mouse monoclonal | (74) |
| RECA-1[1] | Endothelium | Mouse monoclonal | (75) |
| OX43 (Serotec) | Endothelium | Mouse monoclonal | (76) |
| PS040 (Sanblo, Uden. The Netherlands) | Laminin | Rabbit polyclonal | (77) |
| αFibronectin[2] | Fibronectin | Rabbit polyclonal | (78) |
| αType III collagen (SBA, Birmingham, AL, USA) | Type III collagen | Goat polyclonal | (79) |
| αType VI collagen (SBA) | Type VI collagen | Goat polyclonal | (80) |

[1]RECA-1 was kindly provided by Dr. A. M. Duijvestijn, Dept. of Immunology, University of Maastricht, The Netherlands.
[2]αFibronectin was kindly provided by Dr. P. K. Das. Laboratory of Pathology, University of Amsterdam.

Morphometry

For calculation of the number and percentage volume of tumors in each liver lobe, the 8 micron thick sections were analyzed morphometrically using a Quantimet Q500 (Leica, Cambridge, UK) after staining with the lectin Ulex for the detection of cancer cells. The number of tumors was expressed per unit volume of liver tissue ±standard error of the mean or as ratio of the number of tumors in FMK-treated rats and those in untreated rats (×100). The percentage volume of tumors was expressed as the ratio of the volume of tumors and the total volume of the liver tissue including tumors ±standard error of the mean. Statistical analysis was performed with the 2-tailed Mann-Whitney test using the software program JPM (SAS Institute, Cary, N.C.).

Biochemical Analysis

Cathepsin B activity was determined in homogenates obtained from each individual liver lobe of all rats according to Cox and Eley (56) with the use of the fluorogenic substrate CBZ-Ala-Arg-Arg-7-amino-4-trifluoromethylcoumarin (Enzyme Systems Products, Dublin, Calif.).

Results—Catheosin B Activity in Cancer Cells

Cathepsin B protein activity localize in the cancer cells. Immunocytochemical analysis revealed that cathepsin B molecules were present at or near the plasma membrane of CC531 cancer cells (FIG. 9A). FIG. 9B shows in a reconstructed 3D CSLM image that cathepsin B was bound to the plasma membrane and active extracellularly at the physiological pH of PBS in which the cells were kept alive. The contours of the cells were made non-transparent (opaque) with the use of the 3D visualization program. This procedure enabled us to visualize only extracellular cathepsin B activity. On the basis of this 3D reconstruction we concluded that cathepsin B was present at the outside of the cancer cells. In contrast, living hepatocytes showed activity only in intracellular granules in the bile canalicular areas of the cells (FIG. 9C). These granules are probably lysosomes. It can be concluded that the proteolytic activity at the plasma membrane of cancer cells, which is responsible for liberation of cresyl violet, is cathepsin B activity because (a) the enzyme was localized at the plasma membrane with a specific antibody against cathepsin B (FIG. 9A) and (b) the selective water-soluble cathepsin B inhibitor FMK (40,53) inhibited the plasma membrane-bound activity completely (FIG. 9D). This selective inhibition of plasma membrane-bound activity becomes particularly clear when comparing FIGS. 9D and 9E. FIG. 9E shows one of the optical CSLM sections that were used for the 3D reconstruction in FIG. 9B.

Referring now to FIG. 9 is shown Cathepsin B expression in rat colon cancer cells (CC531) and hepatocytes. (9A) Photomicrograph of immunolocalization of cathepsin B on CC531 cells. Cathepsin B proteins was present close to or at the plasma membrane (arrowheads). Bar=3 $\mu$m. (9B) Digital 3D reconstruction of living CC531 cells incubated for 5 min. at room temperature in PBS containing 10 $\mu$m [Z-Arg]$^2$-cresyl violet and imaged by CSLM. The periphery of cells is demonstrated in red and fluorescence of cresyl violet in gold represents cathepsin B activity. Activity was present in patches (large arrowheads) and small spots (small arrowheads) at the outside of the cell periphery. Confocal data stack of 26 optical sections, approx. 0.5 $\mu$m thick, was processed with a 3D visualization computer program AVS. Bar=3 $\mu$m. (9C) Digital CSLM optical section, 0.5 $\mu$m thick, of a living isolated rat hepatocyte incubated for 5 min. at room temperature in PBS containing 10 $\mu$m [Z-Arg]$^2$-cresyl violet. Fluorescence of cresyl violet was produced by cathepsin B-like activity which was present in granular lysosome-like intracellular compartments (arrowheads). Bar=3 $\mu$m. (9D) Digital CSLM optical section, 0.5 $\mu$m thick, of living CC531 cells incubated for 5 min. at room temp. in PBS containing 10 $\mu$m [Z-Arg]$^2$-cresyl violet and 20 $\mu$m of the selective cathepsin B inhibitor FMK. Activity was present intracellularly (small arrowheads) but not at the plasma membrane (large arrowheads). Plasma membrane-bound activity was inhibited by FMK>Bar=2 $\mu$m. (9E) Digital CSLM optical sections, 0.5 $\mu$m thick, of living CC531 cells incubated fro 5 min. at room temperature in PBS containing 10 $\mu$m [Z-Arg]$^2$-cresyl violet. Fluorescence of cresyl violet is found at the plasma membrane (large arrowheads) and intracellularly (small arrowheads). Bar=5 $\mu$m.

Colon Cancer Metastasis in Rat Liver

One week after CC531 cells had been administered to rats, livers contained tumors of variable size (FIG. 10). The three large lobes contained on average one or two tumors per unit volume of liver whereas the small caudate lobe contained three times as many (Table 2). Treatment of rats with 20 mg FMK per kg body weight per day during one week before until one week after administration of the cancer cells reduced the number of tumors on average by 60% in the large lobes. The number of tumors in the caudate lobe was increased rather than decreased, although the difference was not significant (Table 2). As a result, 20-fold larger number of tumors per unit volume of tissue was found in the caudate lobe than in the other lobes. Treatment with the inhibitor reduced the total volume of tumors in the large lobes on average by 80% (Table 3). The average size of tumors in the large liver lobes of animals treated with the inhibitor was 40% of their size in untreated animals. In the caudate lobe, the size of tumors was not affected by treatment (cf. Tables 2 and 3). The overall effect of treatment with the cathepsin B inhibitor in the entire liver was a reduction of the mean number of tumors by 35% and the mean volume by 57%, when the relative sizes of the liver lobes are taken into account on the basis of their wet weight (the left lateral, median, right lateral and caudate lobes represent 33,34,23 and 10% of the total liver, respectively).

TABLE 2

Numbers of colon cancer tumors found in different liver lobes of rats untreated (−FMK: n = 16) or those treated orally with 20 mg FMK per kg body weight daily for 14 days (+FMK: n = 16)

| Liver Lobes | −FMK | +FMK | % |
|---|---|---|---|
| Left lateral | 2.1 ± 0.7 | 0.5 ± 0.2 | 24 |
| Median | 1.7 ± 0.6 | 0.4 ± 0.2 | 24 |
| Right lateral | 1.1 ± 0.6 | 1.0 ± 0.4 | 91 |
| Caudate | 5.1 ± 2.2 | 14.2 ± 7.5 | 278 |

The number of tumors is expressed per unit volume of liver tissue ± SEM or as the ratio of the number of tumors in treated rats compared with untreated rats (×100; %) as determined morphometrically in 8 μm thick cryostat sections stained with the lectin Ulex europaeus agglutinin I. Differences in number of tumors in left lateral and median lobes but not in right lateral and caudate lobes between treated and untreated animals were significant (P=0.006 and P=0.1, respectively). Differences in number of tumors between the three large lobes and the caudate lobe were not significant in untreated animals (P=0.06) but highly significant in treated animals (P=0.003).

TABLE 3

Percentage volume of colon cancer tumors in different liver lobes of untreated rats (−FMK: n = 16) or those treated orally with 20 mg FMK per kg body weight daily for 14 days (+FMK: n = 16)

| Liver Lobes | −FMK | +FMK | % |
|---|---|---|---|
| Left lateral | 8.3 ± 4.1 | 1.4 ± 0.5 | 17 |
| Median | 9.9 ± 8.3 | 0.3 ± 0.6 | 3 |
| Right lateral | 3.3 ± 2.0 | 1.1 ± 0.2 | 35 |
| Caudate | 17.6 ± 9.2 | 49.8 ± 38.5 | 283 |

The percentage voume of tumors is expressed as the ratio of the volume of tumors and total volume of the liver tissue including tumors (×100)± SEM as determined morphometrically as described for Table 2. The ratio of percentage volumes in treated rats and untreated rats (×100) is also given (%). Differences in percentage volume of tumors in the three large liver lobes but not in the caudate lobe between untreated and treated rats were significantly different (P<0.05 and P=0.8, respectively). Differences in percentage volume of tumors between the large lobes and the caudate lobe were not significant in untreated rats (P=0.07) but highly significant in treated rats (P=0.001).

Whether or not the two weeks of oral treatment with the inhibitor had the same effect on cathepsin B activity in all liver lobes was determined. Biochemical analysis revealed that activity (0.035±0.005 U/mg protein) and inhibition (51±14%) were similar in all four lobes. The host defense against cancer cells in the liver which is mainly realized by Kupffer cells and pit cells (52) was also similar in all four lobes; numbers and activation state of both cell types as determined by immunohistochemical analysis (Table 1) were comparable in all lobes.

Significant differences between the caudate lobe and the other liver lobes with respect to the endothelial compartment or distribution patterns of extracellular matrix compounds (see Table 1 for specification of parameters investigated) could not be detected either. Treatment with FMK did not affect body weight, total liver weight or the weight of the individual lobes (data not shown).

In one embodiment, the present invention demonstrates that (a) this in vivo model for metastasis is an excellent tool to analyse a number of steps of metastasis of colon cancer in this environment and to manipulate therapeutically this complex malignant process; (b) heterogeneity exist between liver lobes with respect to environmental conditions for colon cancer cells to invade and grow; (c) the colon cancer cell line that is able to grow in the liver possesses functionally active cathepsin B at the outside of the plasma membrane under physiological conditions; (d) in vivo treatment with a selective inhibitor of extracellular cathepsin B reduces the number and size of tumors in rat liver except for the caudate lobe. These results are extrapolated to colon cancer metastasis in the human liver, so that single lobe hepatectomy followed by therapy with proteinase inhibitor is indicated.

Discussion Concerning Dipeptidyl Peptidase IV (DPPIV)

A new type of fluorogenic susbtrates for proteases based on the leaving group cresyl violet has been synthesized. Cresyl violet is not fluorescent when amino acids or peptide groups are attached but becomes highly fluorescent after proteolytic liberation. Its fluorescence shows linearity with concentration and hardly any fading. Properties of Ala-Pro-cresyl violet as substrate for dipeptidyl peptidase IV (DPPIV) (CD26) for localization and quantification of its activity in individual freshly isolated living rat hepatocytes were investigated using confocal microscopy, image analysis and flow cytometry. DPPIV activity was localized exclusively in patches at plasma membranes likely being bile canalicular domains. Activity was analyzed quantitatively in individual cells by capturing series of images in time. Production of fluorescence was analyzed on the basis of the series of digital images and it appeared to be nonlinear with time. By calculation of the initial velocity at time zero, activity of DPPIV per individual hepatocyte was calculated. Cresyl violet-dependent fluorescencee appeared in a similar way when cells were analyzed by flow cytometry. A dipeptide phosphonate inhibitor inhibited production of fluorescence competitively with a $K_i$, of 7 μM. $K_m$ values in individual hepatocytes varied in the range of 6–22 μM depending on the individual rat from which the hepatocytes were obtained, whereas the $V_{max}$ varied in the range of 4–16 nU. $K_m$ and $V_{max}$ values per individual rat were inversely correlated indicating posttranslational regulation of the kinetic parameters of DPPIV. This relationship was lost when membrane fractions of the same hepatocyte suspensions were analyzed. It is concluded that cresyl violet-based protease substrates are the compounds of choice to localize and quantify protease activity in living cells and tissues.

The kinetic parameters of DPPIV in individual living hepatocytes were investigated to establish the possibilities of the use of fluorogenic cresyl violet-based substrate in combination with digital imaging techniques for in vivo analysis of enzyme function. Images were captured continuously in time while the reaction and thus generation of fluorescence in the cells proceeded. Analysis of series of these images provided quantitative information of the enzyme reaction as a function of time per individual cell.

Results and Discussion for Dipeptidyl Peptidase IV

The localization properties of cresyl violet in individual cells were investigated using confocal microscopy. FIG. 3 is a 3D representation of individual living hepatocytes incubated for 5 min in Krebs-Henseleit buffer containing 10 μM substrate. The fluorescence is localized only in patches at the plasma membrane. Because DPPIV is an ectoprotease that is localized at the apical bile canalicular membrane, these patches are likely bile canalicular membrane domains. It shows that cresyl violet fluorescence represents sites of activity of enzymes in intracellular domains. This good localization in combination with the fact that excitation can be performed at a relatively long wavelength (568 nm) to avoid photochemical damage to the living cells make cresyl violet-based fluorogenic substrate excellent tools for living cell cytochemistry. The only other type of synthetic protease substrates that has been applied so far to living cells are rhodamine-based (37A,A38). These substrates have several disadvantages in comparison with cresyl violet-based substrates due to the low water-solubility (39A,40A) and the tendency of the rhodamine leaving group to accumulate in mitochondria of living cells after proteolytic cleavage (41 A) which limit their usefulness for living cell cytochemistry. Furthermore, rhodamine-based substrates for cathepsin B are not very specific because of the large size of the substrates for cathepsin B are not very specific because of the large size of the rhodamine leaving group (39A,40A). Rhodamine-based substrates are suitable for flow cytometric analysis of protease activity in living cells (17A,40A, 42A,43A) or virus particles (44A) provided low substrate concentrations are used which hampers the determination of kinetic parameters of enzymes (39A,40A). The exact intracellular localization (FIG. 3) in combination with the quantitative properties (FIG. 2) prove that cresyl violet has excellent properties as a leaving group for quantitative cytochemical analysis using confocal microcopy (FIG. 3), image analysis (FIGS. 4–7) and flow cytometry (FIG. 8). Prolonged periods of incubation resulted in diffusion of cresyl violet from the cells but the first 5 min of incubation could be used safely for intracellular localization and quantification without introducing errors by diffusion. We also tried to employ cresyl violet-based substrates for visualization to protease activity in cells after freezing and thawing and in unfixed cryostat sections but these efforts were without success due to rapid diffusion of cresyl violet from sites where it was produced. Apparently, the high quality localization characteristics of cresyl violet are very much dependent on the vital status of cells. Cresyl violet-based substrates can be applied to show protease activity in cultured tissues. Such application indicates that the viability of cells is essential for a successful application of cresyl violet-based substrates. Cresyl violet-based substrates penetrate living cells as was shown in parallel experiments using [CBZ-Arg]$^2$-cresyl violet to demonstrate lysosomal cathepsin B activity in living hepatocytes and colon cancer cells (13A,45A). On the basis of these studies of intralysosomal cathepsin B activity and FIG. 3, it can be concluded that production of fluorescence on the plasma membrane of hepatocytes incubated in the presence of [Ala-Pro]$^2$-cresyl violet represents the exact localization of DPPIV activity.

When 2D images of cells were captured in time and formation of fluorescence was analyzed, plots like the one in FIG. 4A were obtained. There was no signal obtained when cells were incubated in the absence of substrate. Autofluorescence was very low or even absent because emission was captured at >595 nm. These plot enabled the calculation of initial velocities ($V_{ini}$) as described previously for quantitative chromogenic enzyme cytochemical methods (4A,33A). When the reactions were analyzed fluorometrically using suspensions of living hepatocytes or membrane fractions of hepatocytes or membrane fractions of hepatocytes, similar plots were obtained (FIGS. 4B and C). $V_{ini}$ was taken as a measure of DPPIV activity in cells. Variation of substrate concentration revealed Michaelis-Menten kinetics of DPPIV in individual hepatocytes (FIG. 5). The intercellular variation of DPPIV activity in an individual rat was rather constant (the standard error of the mean was in the range of 10–20 per cent irrespective the substrate concentration. This variation is visualized in FIG. 8B (see below).

The effects of the selective competitive dipeptide phosphonate inhibitor are shown in FIG. 6. It indicates the selective visualization of DPPIV activity with Ala-Pro-cresyl violet as substrate. The $K_i$ was 7 $\mu$M. When calculating $V_{max}$ and $K_m$ values from the data in FIG. 5, it appeared that there was a strong inverse correlation between $K_m$ and $V_{max}$ per individual rat (FIG. 7). When the $V_{max}$ was low, the $K_m$ was high and vice versa. This phenomenon has important implications for the activity of DPPIV at physiological substrate concentrations. The conversion rate in the rat with the highest $V_{max}$ and lowest $K_m$ can be 10- to 20-fold higher than in the rat with the lowest $V_{max}$ and the highest $K_m$. It suggests that there is posttranslational regulatory control of DPPIV activity in hepatocytes. Flow cytometric analysis of the enzyme reaction in individual hepatocytes is shown in FIG. 8. FIG. 8A is a plot of Heochst fluorescence versus scatter. This allowed us to select the population of living cells. The reaction of DPPIV in time; in the selection of living hepatocytes is shown in FIG. 8B. This figure indicates the intercellular variation of activity.

The present invention demonstrates that: a) cresyl violet-based substrates have great potential to visualize and quantify activity of protease in individual living cells. These substrates allow a very precise localization of active fractions of protease in intracellular compartments when applying confocal microscopy. Quantitative determination of the active fraction in individual cells can be obtained by applying image analysis or in cell populations when flow cytometry is used; b) Ala-Pro-cresyl violet demonstrates specifically DPPIV activity at the bile canalicular membrane domain of freshly isolated rat hepatocytes; c) and DPPIV shows activity that is regulated strongly posttranslationally in the sense that there is an inverse correlation between $V_{max}$ and $K_m$ indicating that when needed both capacity and affinity can be upregulated. This regulation may occur by glycosylation and/or sialylation. This dynamic aspect of the enzyme was lost when membrane fractions were analyzed.

This novel fluorogenic indicator is also useful to determine activity in various cells or tissues. See below.

Caspase Inhibitors Substrates

| Caspase Inhibitors Number | Substrate (Cresyl violet substituted) | |
|---|---|---|
| 1. | A-Tyr-Val-Ala-Asp-, | (SEQ. ID NO: 3); |
|  | A-Trp-Glu-His-Asp-, | (SEQ. ID NO: 4); |
| 2. | A-Val-Asp-Val-Ala-Asp-, | (SEQ. ID NO: 5); |
|  | A-Val-Asp-Glu-Gln-Asp-, | (SEQ. ID NO: 6); |
| 3. | A-Asp-Glu-Val-Asp-, | (SEQ. ID NO: 7); |
| 4. | A-Leu-Glu-Val-Asp-, | (SEQ. ID NO: 8); |
| 5. | A-Trp-Glu-His-Asp-, | (SEQ. ID NO: 9); |
| 6. | A-Val-Glu-Ile-Asp-, | (SEQ. ID NO: 10); |
|  | A-Val-Gln-Val-Asp-, | (SEQ. ID NO: 11); |
| 7. | A-Asp-Glu-Val-Asp-, | (SEQ. ID NO: 12); |

-continued

Caspae Inhibitors Substrates

| Caspase Inhibitors Number | Substrate (Cresyl violet substituted) | |
|---|---|---|
| 8. | A-Ile-Glu-Thr-Asp-, | (SEQ. ID NO: 13); |
| 9. | A-Leu-Glu-His-Asp-, | (SEQ. ID NO: 14); |
| 10. | A-Asp-Glu-Val-Asp; | (SEQ. ID NO: 15); |
|  | A-Val-Ala-Asp; or |  |
|  | A-Ile-Glu-Pro-Asp wherein A = CBZ or Ac | (SEQ. ID NO: 16), |

The following examples are provided to be descriptive and explanatory only. They are not to be construed to be limiting in any way.

Materials and Methods

EXAMPLE 1

Synthesis of [Ala-Pro]$^2$-cresyl violet

Z-alanyl-proline dicyclohexylamine salt (5 g, 10 mmole) was suspended in 80 ml dimethylformamide/pyridine (1:1 v/v) and cooled to 0° C. Then, 1-(3-methylaminopropyl)-3-ethylcarbodiimide hydrochloride (2 g, 10.4 mmole) was added. After 20 min at 0° C., cresyl violet hydrochloride (1 g, 3.2 mmole) was added. The reaction mixture was allowed to stir 18 h while the temperature was raised slowly to room temp. The solvents were removed at 50° C. and the residue was dissolved in 300 ml ethyl acetate. The solution was washed twice with 100 ml 1 N aqueous hydrochloric acid, once with 50 ml saturated aqueous brine, twice with 100 ml saturated aqueous sodium bicarbonate, and once with 100 ml saturated aqueous brine. The ethyl acetate solution was dried over anhydrous magnesium sulfate, filtered, stripped on a rotary evaporator and dried overnight under high vacuum. The crude product (1.5 g) was chromatographed on silica gel using 5% (v/v) methanol in methylene chloride and then on LH-20 eluting with methanol. The purified product, [Ala-Pro]$^2$-cresyl violet, weighed 0.9 g (33%). It was then treated at room temp for 1 h with 10 ml of 30% (w/v) hydrogen bromide in acetic acid. The reaction mixture was added to 200 ml diethyle ether. The precipitated substrate, [Ala-Pro]$^2$-cresyl violet dihydrobromide, was filtered, washed with ether and dried under high vacuum. The yield was 0.84 g. Thin layer chromatography on silica gel with butanol/acetic acid/water (4:1:1) showed a single brown spot at Rf=0.05 that was not fluorescent by itself but was red fluorescent after strong heating. The chemical structures of the nonfluorescent substrate, the fluorescent product, cresyl violet, and the cleavage sites for DPPIV are shown in FIG. 1.

EXAMPLE 2

Isolation of Hepatocytes

Hepatocytes were isolated by collagenase perfusion of livers of male Wistar rats (200–250 g; HSD Animal Farm, Zeist, The Netherlands) after 24 h of starvation as described previously (30). The animals were exposed to a controlled dark-light cycle (light: 7:00 a.m.–7:00 p.m.) throughout the acclimatization period of at least 1 week. Before starvation, animals had free access to food (standard chow diet; Hope Farms, Woerden, The Netherlands) and water. The animals had always free access to water. During operation, the animals were under Nembutal anaesthesia. Animal care was performed according to the guidelines of the University of Amsterdam. Hepatocytes (5–10 mg dry mass/ml) were kept in Krebs-Henseleit bicarbonate medium containing 1.3 mM $Ca^{2+}$, 10 mM sodium Hepes (pH 7.4), 20 mM glucose and 1 mM octanoate on ice until enzyme assays. Homogenates were prepared by freezing cell suspensions in liquid nitrogen and subsequent thawing. One volume of homogenates and 10 volumes of 20 mM Tris-HCI buffer (pH 7.4) containing 1% (v/v) Triton X-100 were mixed and incubated at 4° C. under constant stirring for 60 min. One part of these homogenates was used for the determination of DPPIV activity. Another part was centrifuged (40,000 x g, 4° C., 20 min) and the supernatants were used as membrane fractions for the determination of DPPIV activity.

EXAMPLE 3

Analysis of DPPIV Activity

DPPIV activity was determined in hepatocytes using 6 approaches. Activity was determined in living hepatocytes with confocal scanning laser microscopy, image processing and analysis, flow cytometry, and fluorometry. Fluorometry was also used for the determination of activity in homogenates of hepatocytes and in membrane fractions of hepatocytes. Incubations were started at t=0 by adding an aliquot of 60 µl hepatocytes to 3 ml Krebs-Henseleit medium containing 0–50 µM (Ala-Pro)$^2$-cresyl violet in the presence or absence of 0–50 µM Ala-Pip$^P$(OPh-4-Cl)$_2$ (Enzyme Systems Products), which is a selective DPPIV inhibitor (31A, 32A). Substrate and inhibitor were dissolved first in dimethylsulfoxide. The final concentration of dimethylsulfoxide in the incubation medium was 0.5% (v/v). Incubations were carried out at 20° C. Confocal scanning laser microscopy was performed after 100 µl of an assay medium containing hepatocytes was brought into a well formed by a stainless steel ring attached to a glass slide (33A). Images of cells were captured in time with a Leica confocal scanning laser microscope fitted to a Leica Fluovert inverted microscope equipped with a PL APO oil-immersion objective (63x, NA 1.40). Excitation was performed at 568 nm and fluorescence was captured at >595 nm. The pinhole aperture was set to provide an optimized image (34A). Cells were subjected to optical serial sectioning after each 60 sec of incubation up to 300 sec. Images in the X-Y plane were recorded with intervals of 0.5 µm in the Z direction. Each optical section was averaged 8 times. Images were recorded din a 512×512 pixel format. The size of each pixel represented 0.015 µm$^2$ in the object. Confocal data stacks of 20–30 optical sections were processed with standard Leica software package.

Image analysis was performed by transferring an aliquot of 100, µl of an incubation medium containing hepatocytes into an incubation chamber that consisted of an object glass and a cover glass separated by a spacer made of adhesion tape with a thickness of 40 µm. The object glass was set on the stage of a fluorescencee microscope (Leitz Dialux 20, Wetzlar, Germany) with a x25 objective (NA 0.75). A drop of medium was placed beside the cover glass and the chamber became filled by capillary forces in a few seconds. The first image was captured at 15–30 sec after the reaction was started using a CCD camera with an 8-bit resolution (Cohu 4910; San Diego, Calif., USA), frame grabber (LG-3, Scion; Frederick, Md., USA), and a Power Macintosh 8100/110 computer (Apple, Cupertino, Calif., USA), using the public domain NIH imaging software program (version 1.57; written by Wayne Rassband and available via Internet by anonymous ftp from zippy.nimh.nih.gov). Settings of camera and frame grabber were according to Jonker et al. (35A). A parabolic curve was fitted to the data per hepatocyte over time using a least-squares curve-fitting method (Mac Curve Fit 1.2d4 program; MCF, Shareware by Kevin Raner, Internet: kraner@asclink.net.au) (4A,33A). In this function, $f(t)=at^2+bt+c$, coefficient a represents the time-dependent deviation from the initial reaction rate, b the initial reaction rate ($V_{ini}$) and c the fluorescence at t=0. $V_{ini}$ values were used as measure of DPPIV activity. These values were plotted against substrate concentration. A hyperbolic curve was fitted to the data with the use of the MCF program and $V_{max}$ and $K_m$ values were determined.

Calibration was performed by measuring fluorescence of a series of solutions of 0–10 $\mu$M cresyl violet in Krebs-Henseleit medium. These solutions were also used to test the properties of cresyl violet for quantitative purposes. The depth of the incubation chamber was 24 $\mu$m and the size of the area measured 240×170 $\mu$m. The total volume that was measured was thus 0.001 $\mu$l. The amount of fluorescence captured by image analysis was linearly related with concentrations up to at least 10 $\mu$M when measured in a thin film of 24 $\mu$m which approximates the diameter of cells (FIG. 2A). Fading did not occur to any significant extent during measurements in time as is shown in FIG. 2B. Thus, cresyl violet has fluorescence properties that are necessary for quantitative fluorescence microscopy (36B). On the basis of FIG. 2A, it was calculated that 100 gray values corresponded with 6.7 fmoles cresyl violet. From these data, DPPIV activity could be calculated in absolute enzyme units (1 U=1 $\mu$mole cresyl violet produced per min). Flow cytometric analysis of production of cresyl violet in hepatorcytes was performed with a FAC-Star Plus (Becton and Dickinson, San Jose, Calif., USA) using the software program CellQuest (version 1.0; Becton and Dicksinson). Prior to analysis, cells were stained with the DNA dye Hoechst 3.3.3.4.2 (36 $\mu$g/ml; Hoechst Holland, Amsterdam, The Netherlands) for 30 min at 0° C. Analysis was started by established forward scatter and then substrate was added at t=0. Analysis was performed at a flow rate of 200 cells/sec. The parameters measured were time, forward scatter, fluorescence of Hoechst 3.3.3.4.2 dye (excitation at 350 nm, emission at 485 nm with a band width of 20 nm), and fluorescence of cresyl violet (excitation at 514 nm, emission at 630 nm with a band width of 22 nm). Filters were obtained from Becton and Dickenson. The power of the lasers was set at 200 W. Fluorometric analysis with time was carried out with a Perkin-Elmer LS 50 fluorescence spectrometer (Perkin-Elmer, Gouda, The Netherlands) under continuous magnetic stirring. Cuvettes with a light path of 1 cm were used. Excitation was performed at 591 nm with a slid width of 10 nm and emission was measured at 628 nm (slid width 10 nm). The first measurement was made at 5 sec after mixing cells and incubation medium.

Detailed Description of FIGS. 1–8.

FIG. 1 shows chemical structures of the fluorogenic substrate, [Ala-Pro]$^2$-cresyl violet and the fluorescent product, cresyl violet, after cleavage by DPPIV (large arrows).

FIG. 2 shows the relationship between fluorescence (gray values) and concentration of cresyl violet ($\mu$M) in a 24 $\mu$m thick incubation chamber (A) and between fluorescence and incubation time (B) as determined by image analysis.

FIG. 3 is a 3D Representation of cresyl violet generated in individual living rat hepatocytes after 5 min of incubation in a medium containing 10 $\mu$M Ala-Pro-cresyl violet. This stereopair was made by merging the +5° and −5° projections of a stack of 27 consecutive confocal sections with a scanned area of 74 $\mu$m×74 $\mu$m and collected at 1 $\mu$m intervals in the Z direction. Fluorescent reaction product is generated exclusively at the cell membranes.

FIG. 4A shows the formation of cresyl violet fluorescence in a single hepatocyte as function of time in the presence (○) or absence (●) of 10 $\mu$M Ala-Pro-cresyl violet as measured with image analysis.

FIG. 4B shows the reaction in suspensions of hepatocytes and FIG. 4C in membrane fractions as measured with fluorometry. Cells and substrate were mixed at t=0 as indicated by arrow. The derivative at t=0 of the quadratic function representing the reaction rate yielded initial velocity ($V_{ini}$).

FIG. 5 shows the relationships between initial velocity of DPPIV ($V_{ini}$ expressed in nU activity) in living hepatocytes and the Ala-Pro-cresyl violet concentrations in the incubation medium for 5 individual rats. Each measuring point represents the mean $V_{ini}$ of 10 individual hepatocytes as determined with image analysis.

FIG. 6 shows the characteristics of inhibition of DPPIV activity in individual living hepatocytes by the selective competitive inhibitor Ala-Pip$^P$(OPh-4Cl)$_2$ as determined by image analysis. Each measuring point is the mean value of 10 individual hepatocytes.

FIG. 7 shows the inverse relationship between $K_m$ in $\mu$M and $V_{max}$ in nU of DPPIV in individual living hepatocytes of 5 individual rats.

FIG. 8 is a flow cytometric analysis of DPPIV activity in individual hepatocytes using Ala-Pro-cresyl violet as substrate. A) Analysis of Hoechst 3.3.3.4.2. fluorescence (DNA dye) versus forward scatter in a selection of intact living cells characterized by low fluorescence and high forward scatter (window indicated by white oval). B) Selection of hepatocytes in A showing generation of fluorescence of cresyl violet as a function of time using 10 $\mu$M Ala-Pro-cresyl violet which was added at t=0 as indicated by arrow.

While only a few embodiments of the invention have been shown and described herein, it will become apparent to those skilled in the art that various modifications and changes can be made in the method using amino acid substituted cresyl violet and the kit containing it as an indicator for tissue or cells without departing from the spirit and scope of the present invention. All such modifications and changes coming within the scope of the appended claims are intended to be carried out thereby.

We claim:

1. A method to detect the presence of an enzyme in living individual cells, which method comprises:
   (a) obtaining living individual cells to be analyzed;
   (b) contacting the living individual cells with a substrate of the structure:

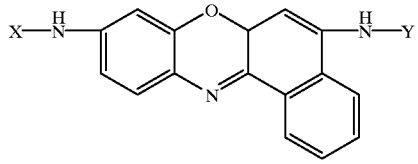

wherein
   X is selected from one or more natural or synthetic amino acids with or without amino blocking groups,
   Y is selected from one or more natural or synthetic amino acids with or without amino blocking groups,
   wherein X and Y are the same or different and are amino acid sequences of between about 1 to 1,000,000 amino acids wherein each amino acid is the same or a different amino acid;
   wherein when an enzyme which degrades X or Y is present in the living individual cells, m fluorescent cresyl violet is released producing a color change wherein the color produced remains within the living individual cells;
   (c) detecting the presence and amount of the enzyme present by the detection and quantification of fluorescence produced; and
   (d) comparing the fluorescence to a pre-calibrated fluorescence scale to quantify the fluorescence present.

2. The method of claim 1 wherein the amino acid sequences X and Y are independently between about 1 and about 10,000 amino acids.

3. The method of claim 1 wherein the amino acid sequences X and Y are independently between about 1 and about 100 amino acids.

4. The method of claim 1 wherein the amino acid sequences are independently between about 1 and about 10 amino acids.

5. The method of claim 1 wherein X is the same as Y or X is different from Y, and X has 1 to 1000 amino acids, and Y has 1 to 1000 amino acids, wherein X and Y are each independently selected from synthetic amino acids or natural amino acids, which natural amino acids are selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

6. The method of claim 1 wherein the amino acid sequences optionally having blocking groups are independently selected from the group consisting of Ala-pro, A-arg-, A-asp-glu-val-asp-, A-ile-glu-thr-asp, A-Tyr-Val-Ala-Asp; A-Trp-Glu-His-Asp; A-Val-Asp-Val-Ala-Asp; A-Val-Asp-Glu-Gln-Asp; A-Asp-Glu-Val-Asp; A-Leu-Glu-Val-Asp; A-Trp-Glu-His-Asp; A-Val-Glu-Ile-Asp; A-Val-Gln-Val-Asp; A-Asp-Glu-Val-Asp; A-Ile-Glu-Thr-Asp; A-Leu-Glu-His-Asp; A-Asp-Glu-Val-Asp; A-Val-Ala-Asp; and A-Ile-Glu-Pro-Asp, wherein A- is selected from carbobenzoxy and acetyl.

7. The method of claim 5 wherein X and Y are each between 1 and 5 amino acids.

8. The method claim 1 wherein the living individual cells are mammalian.

9. The method of claim 1 wherein the living individual cells are from a human being.

10. A method to detect the presence of a protease enzyme in living individual cells, which method comprises:
    (a) obtaining living individual cells to be analyzed;
    (b) contacting living individual cells with a substrate of the structure:

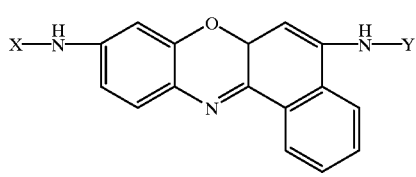

wherein X and Y are each ala-pro-, with or without amino blocking groups;
    wherein when an enzyme which degrades X or Y is present within the living individual cells; fluorescent cresyl violet is released producing a color change wherein the color produced remains within the living individual cells;

(c) detecting the presence and amount of the enzyme present by the detection and quantification of fluorescence produced; and (d) comparing the fluorescence to a pre-calibrated fluorescence scale to quantify the fluorescence present.

11. The method claim 10 wherein the living individual cells are mammalian.

12. The method of claim 10 wherein the living individual cells are from a human being.

13. A diagnostic kit to determine the presence of an enzyme in living individual cells, which kit comprises:

a substrate of the structure:

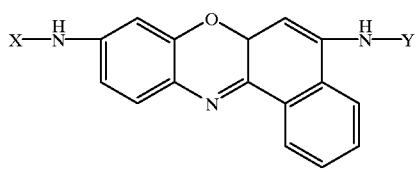

wherein

X is selected from one or more natural or synthetic amino acids with or without amino blocking groups, Y is selected from one or more natural or synthetic amino acids with or without amino blocking groups, wherein X, Y, and combinations thereof is at least one amino acid and is between about 1 and 100 amino acids which amino acids are degraded in the presence of an enzyme within living individual cells to release free fluorescent cresyl violet which is detected within said living individual cells and quantified.

14. The kit of claim 11 wherein the enzyme detected is a protease.

15. The kit of claim 13 wherein X=Y or X does not equal Y and X of 1 to 100 amino acids and Y of 1 to 100 amino acids are each independently selected from the group consisting of synthetic amino acids or natural amino acids wherein said natural amino acids are selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

16. The kit of claim 13 wherein X is equal to Y and each is selected from the group consisting of alanyl-proline, Z-arg, A-Tyr-Val-Ala-Asp; A-Trp-Glu-His-Asp; A-Val-Asp-Val-Ala-Asp; A-Val-Asp-Glu-Gln-Asp; A-Asp-Glu-Val-Asp; A-Leu-Glu-Val-Asp; A-Trp-Glu-His-Asp; A-Val-Glu-Ile-Asp; A-Val-Gln-Val-Asp; A-Asp-Glu-Val-Asp; A-Ile-Glu-Thr-Asp; A-Leu-Glu-His-Asp; A-Asp-Glu-Val-Asp; A-Val-Ala-Asp; and A-Ile-Glu-Pro-Asp, wherein A is selected from CBZ and Ac.

17. The kit of claim 16 wherein X is equal to Y and each is alanyl-proline or Z-arginine.

18. A diagnostic kit to determine the presence of an enzyme in living individual cells, which kit comprises:

a substrate of the structure:

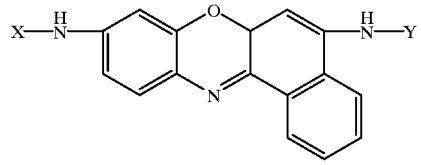

wherein

X and Y are each Ala-Pro- with or without amino acid blocking groups, which Ala-Pro groups are degraded in the presence of a protease enzyme to release free fluorescent cresyl violet which remains within the living individual cells wherein said cresyl violet is detected within said living individual cells and quantified.

* * * * *

UNITED STATES PATENT AND TRADEMARK OFFICE
CERTIFICATE OF CORRECTION

PATENT NO. : 6,235,493 B1
DATED : May 22, 2001
INVENTOR(S) : Eugene R. Bissel and Robert F. Smith It is certified that error appears in the above-identified patent and that said Letters Patent is hereby corrected as shown below:

Title page,
Item [73], Assignee, delete "The Regents of the University of California, Oakland, CA (US)" and insert -- Enzyme Systems Products, Inc., Livermore, CA (US)" --

Signed and Sealed this

Sixteenth Day of April, 2002

Attest:

JAMES E. ROGAN
*Attesting Officer*     *Director of the United States Patent and Trademark Office*